US010682403B2

United States Patent
Pretorius et al.

(10) Patent No.: US 10,682,403 B2
(45) Date of Patent: Jun. 16, 2020

(54) MULTI-EPITOPE DNA VACCINE FOR HEARTWATER

(71) Applicant: AGRICULTURAL RESEARCH COUNCIL, Pretoria (ZA)

(72) Inventors: Alri Pretorius, Onderstepoort (ZA); Frederika Elizabeth Faber, Onderstepoort (ZA); Helena Cornelia Steyn, Onderstepoort (ZA); Junita Liebenberg, Onderstepoort (ZA); Mirinda Van Kleef, Onderstepoort (ZA); Nontobeko Thema, Onderstepoort (ZA); Selaelo Ivy Tshilwane, Onderstepoort (ZA)

(73) Assignee: AGRICULTURAL RESEARCH COUNCIL, Pretoria (ZA)

( * ) Notice: Subject to any disclaimer, the term of this patent is extended or adjusted under 35 U.S.C. 154(b) by 0 days.

(21) Appl. No.: 16/472,153

(22) PCT Filed: Dec. 20, 2017

(86) PCT No.: PCT/IB2017/058188
§ 371 (c)(1),
(2) Date: Jun. 20, 2019

(87) PCT Pub. No.: WO2018/116193
PCT Pub. Date: Jun. 28, 2018

(65) Prior Publication Data
US 2019/0307871 A1    Oct. 10, 2019

(30) Foreign Application Priority Data

Dec. 20, 2016   (GB) .................................. 1621732.5

(51) Int. Cl.
| | |
|---|---|
| *C07H 21/04* | (2006.01) |
| *A61K 39/02* | (2006.01) |
| *C07K 14/29* | (2006.01) |
| *A61K 39/00* | (2006.01) |

(52) U.S. Cl.
CPC .......... *A61K 39/0233* (2013.01); *C07K 14/29* (2013.01); *A61K 2039/53* (2013.01); *A61K 2039/552* (2013.01); *A61K 2039/645* (2013.01); *C07K 2317/34* (2013.01)

(58) Field of Classification Search
CPC ................................................ A61K 39/0233
See application file for complete search history.

(56) References Cited

U.S. PATENT DOCUMENTS 4,079,127 A  *  3/1978 Goldstein ........ C07K 14/57581
514/9.7

OTHER PUBLICATIONS

Didierlaurent., A.M., et al., AS04, an Aluminum Salt- and TLR4 Agonist-Based Adjuvant System, Induces a Transient Localized Innate Immune Response Leading to Enhanced Adaptive Immunity, Journal of Immunology 183:6186-97, 2009.
Esteves, I., et al., Protective Killed Ehrlichia Ruminantium Vaccine Elicits IFN-Gamma Responses by CD4+ CD8+ T Lymphocytes in Goats, Veterinary Immunology and Immunopathology 98(1-2):49-57, Mar. 2004.
International Search Report issued in International Patent Application No. PCT/IB2017/058188 dated Apr. 18, 2018.
Konnai, S., et al., DNA Typing for Ovine MHC DRB1 Using Polymerase Chain Reaction-Restriction Fragment Length Polymorphism (PCR-RFLP). Journal of Dairy Science, 86:3362-3365, 2003.
Liebenberg, J., et al., Identification of Ehrlichia Ruminantium Proteins That Activate Cellular Immune Responses Using a Reverse Vaccinology Strategy, Veterinary Immunology and Immunopathology 145(1-2):340-349, Jan. 2012.
McBride, J.W., Molecular and Cellular Pathobiology of Ehrlichia Infection: Targets for New Therapeutics and Immunomodulation Strategies, Expert Reviews in Molecular Medicine 13, Oct. 1, 2011.
Pretorius, A., et al., A Heterologous Prime/Boost Immunisation Strategy Protects Against Virulent E. Ruminantium Welgevonden Needle Challenge But Not Against Tick Challenge, Vaccine 26(34):4363-4371, Aug. 12, 2008.
Pretorius, A., et al., Protection Against Heartwater by DNA Immunisation With Four Ehrlichia Ruminantium Open Reading Frames, Vaccine 25(12):2316-2324, Feb. 13, 2007.
Sebatjane, S.I., et al., In Vitro and In Vivo Evaluation of Five Low Molecular Weight Proteins of Ehrlichia Ruminantium as Potential Vaccine Components, Veterinary Immunology and Immunopathology 137(3-4):217-225, Oct. 15, 2010.
Steyn, H.C., et al., A Quantitative Real-Time PCR Assay for Ehrlichia Ruminantium Using pCS20. Veterinary Microbiology 131:258-65, 2008.
Thema, N., et al., Cellular Immune Responses Induced In Vitro by Ehrlichia Ruminantium Secreted Proteins and Identification of Vaccine Candidate Peptides, Onderstepoort Journal of Veterinary Research 83(1), Aug. 30, 2016.

(Continued)

*Primary Examiner* — Albert M Navarro
(74) *Attorney, Agent, or Firm* — Knobbe, Martens, Olson & Bear LLP

(57) ABSTRACT

Nucleic acids include sequences encoding *Ehrlichia ruminantium* epitopes which induce a CD4 immune response, and sequences encoding *Ehrlichia ruminantium* epitopes which induce a CD8 immune response. Multi-epitope DNA vaccines include the nucleic acids and polypeptides are encoded by the nucleic acids. Methods of eliciting an immune response against heartwater disease in a subject make use of the nucleic acids, multi-epitope DNA vaccines and polypeptides.

19 Claims, 6 Drawing Sheets
Specification includes a Sequence Listing.

(56) References Cited

OTHER PUBLICATIONS

Tshikhudo, N., et al., Preparation and In Vitro Characterisation of Ehrlichia Ruminantium Plasmid DNA and Proteins Encapsulated Into and DNA Adsorbed Onto Biodegradable Microparticles, Ticks Tick Borne Disease 1:186-193, 2010.

Wakeel, A., et al., New Insights Into Molecular Ehrlichia Chaffeensis—Host Interactions, Microbes and Infection 12(5):337-345, May 1, 2010.

* cited by examiner

```
ATGAGGAGGAAGAGCTACGCCGGCTACCAGACCCTGGAATTGGACAAGGTGGAGCTTCCCAA
AACAAGGGCCAGAGAAACTTCTAGCGATATCACCGTGATCAGCGACGGCCCTGGCCCGGGAA
AGGCCGAGGATAAGGTGGTGAAGGCGGCACAGATTCAGGACGTGCCGGGCCCAGGTCCGGGA
GTCGTGTCCATATGTTGCCAGGGCACATCACTGGGAGGATTTTCTGAGGGACCGGGACCAGG
TACTAAATTGAAGAGGATGGGGTACAAGATTTACAACGTGATCTTCGCTGGACCCGGTCCAG
GCCTTGGGTCCTCCATCATGGCCATATTCGGCAAGCTCCCATGGCCAGCCGGACCCGGTCCA
GGGATCGTCAGCTCCGACACTTCTAATAACGGTAGCGTGGCCGAAGAGAACGGGCCCGGCCC
CGGAGTCAATCAGGAGAACCTCGGCCTCATCAACTTCTGGAAAAAGAAACACCATCATCATC
ACCACTGATCGTCGTTTGTCGTTTTGTCGTTGGTTATTTTCCACCATATTGCCGTCTTTTGG
CAATGTGAGGGCCCGGAAACCTGGCCCTGTCTTCTTGACGAGCATTCCTAGGGGTCTTTCCC
CTCTCGCCAAAGGAATGCAAGGTCTGTTGAATGTCGTGAAGGAAGCAGTTCCTCTGGAAGCT
TCTTGAAGACAAACAACGTCTGTAGCGACCCTTTGCAGGCAGCGGAACCCCCCACCTGGCGA
CAGGTGCCTCTGCGGCCAAAAGCCACGTGTATAAGATACACCTGCAAAGGCGGCACAACCCC
AGTGCCACGTTGTGAGTTGGATAGTTGTGGAAAGAGTCAAATGGCTCTCCTCAAGCGTATTC
AACAAGGGGCTGAAGGATGCCCAGAAGGTACCCATTGTATGGGATCTGATCTGGGGCCTCG
GTGCACATGCTTTACATGTGTTTAGTCGAGGTTAAAAAACGTCTAGGCCCCCCGAACCACGG
GGACGTGGTTTTCCTTTGAAAGTTTAAACGCTAGCATGCAAATATTTGTGAAGACACTGACT
GGCAAAACGATTACCCTCGAGGTCGAACCCAGCGACACCATCGAAAACGTGAAGGCTAAGAT
CCAGGACAAGGAGGGTATACCACCTGACCAGCAACGCCTCATCTTCGCGGGGAAGCAGCTTG
AGGACGGGCGCACATTGTCCGACTATAATATCCAGAAGGAGTCAACGCTTCACCTGGTGCTG
AGACTGAGAGGCGCCGACCTCAAAAACAGAACGATTAACATAGGGGTCGAATTCCGGATCCA
GGACGGCGCCGCTTACCACGACAATCTGAACACCAAAGAGTTGTCAATCAGCCTCCGCATCA
AAGCCGCCTACATTCCGCAGGAGAAGGTGATCATCCTTAACAGGTTCCTGCAGGACTATGTT
AACCAGGAAAACCTGGGACTGCACCACCACCATCACCACTAATCGTCGTTTGTCGTTTTGTC
GTT
```

Figure 2

```
TCGTCGTTTGTCGTTTTGTCGTTATGTCCTCTCTTTCCATACTTCACTTGTTGTTGTTATTG
TTGTCACTTCATAGGAGGAAGAGCTACGCCGGCTACCAGACCCTGAAATTTGAGAGGCAGGG
CCCCGGCCCCGGCAACGGTATTAATGACGAAGACCTGGGCGGCATGTACGGGCTCCTGCTCT
TGGGAGGATTCTTTAGTGTGATGGGCCCCGGCCCCGGCGTTGTTATCGTTATGGATCTGTGT
TGTCAAATCGCCGGTCTTCTCTGTGGCCCCGGCCCCGGCGTGAAAAACTATCTGAATCAGCA
TCTCAAGAAGATTATCGACCGCATCAAGCATTCTAACCTCAACGCTATCGGCCCCGGCCCCG
GCCATCATCATCATCATCATTGATCGTCGTTTGTCGTTTTGTCGTTGGTTATTTTCCACCAT
ATTGCCGTCTTTTGGCAATGTGAGGGCCCGGAAACCTGGCCCTGTCTTCTTGACGAGCATTC
CTAGGGGTCTTTCCCCTCTCGCCAAAGGAATGCAAGGTCTGTTGAATGTCGTGAAGGAAGCA
GTTCCTCTGGAAGCTTCTTGAAGACAAACAACGTCTGTAGCGACCCTTTGCAGGCAGCGGAA
CCCCCCACCTGGCGACAGGTGCCTCTGCGGCCAAAAGCCACGTGTATAAGATACACCTGCAA
AGGCGGCACAACCCCAGTGCCACGTTGTGAGTTGGATAGTTGTGGAAAGAGTCAAATGGCTC
TCCTCAAGCGTATTCAACAAGGGGCTGAAGGATGCCCAGAAGGTACCCCATTGTATGGGATC
TGATCTGGGGCCTCGGTGCACATGCTTTACATGTGTTTAGTCGAGGTTAAAAAACGTCTAGG
CCCCCCGAACCACGGGGACGTGGTTTTCCTTTGAAAGTTTAAACGCTAGCATGCAAATATTT
GTGAAGACACTGACTGGCAAAACGATTACCCTCGAGGTCGAACCCAGCGACACCATCGAAAA
CGTGAAGGCTAAGATCCAGGACAAGGAGGGTATACCACCTGACCAGCAACGCCTCATCTTCG
CGGGGAAGCAGCTTGAGGACGGGCGCACATTGTCCGACTATAATATCCAGAAGGAGTCAACG
CTTCACCTGGTGCTGAGACTGAGAGGCGCCATGCGCACCCCCGCACAGTTCCTTGGTATTCT
GCTGCTCTGGTTCCCTGGTATAAAATGTGCCGCTTACGACATCAGAGCGATTCTGTCCGTGG
ACGGGCTGTTTGACAGCAAGGCCGCCGCTTACCATCATCATCATATCATTGATCGTCGTTTG
TCGTTTTGTCGTT
```

Figure 3

MULTI-EPITOPE DNA VACCINE FOR HEARTWATER

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 2019-06-20_Substitute Sequence Listing (for filing)_SPR003.001APC, the date of creation of the ASCII text file is Jun. 20, 2019, and the size of the ASCII text file is 44.3 KB.

BACKGROUND OF THE INVENTION

The present invention relates to nucleic acids comprising sequences encoding *Ehrlichia ruminantium* epitopes that induce a CD4 immune response, and sequences encoding *Ehrlichia ruminantium* epitopes that induce a CD8 immune response. The invention also provides for multi-epitope DNA vaccines comprising the nucleic acids and for polypeptides encoded by the nucleic acids of the invention. The invention also relates to uses and methods of eliciting an immune response against heartwater disease in a subject using the nucleic acids, multi-epitope DNA vaccines and polypeptides described.

Heartwater is a tick borne disease of both wild and domestic ruminants caused by the obligate intracellular organism, *Ehrlichia ruminantium*. It is transmitted by ticks of the *Amblyomma* species and occurs mainly in Sub-Saharan Africa and the Caribbean Islands. Currently there is no safe and effective vaccine. The only commercial vaccine currently in use is the infection and treatment vaccination using live virulent organisms. This method has a number of practical disadvantages and it does not protect against all the field isolates. Thus, there is an urgent need for alternative vaccines. Research on alternative vaccines like inactivated, attenuated and DNA vaccines has been ongoing. With the exception of the attenuated vaccine these have all had limited success in the field.

DNA vaccines consisting of pathogen-derived immunogens could offer a safe and effective alternative to the current vaccine. Work done previously by the Applicant showed that a DNA vaccine encoding four *E. ruminantium* open reading frames could provide 100% protection in sheep following laboratory challenge but failed under field conditions. In the preceding studies, reverse vaccinology was applied in order to identify additional vaccine candidates. Five low molecular weight proteins that could induce antigen specific recall cellular immune responses in immune sheep peripheral blood mononuclear cells (PBMC) were identified. However, when tested as a DNA vaccine only partial protection against laboratory challenge was obtained.

Additional vaccine candidates were identified that could induce upregulation of cytokines associated with innate immunity and adaptive cellular immune responses. It is well documented that a cellular T helper 1 (Th1) immune response is crucial in the protection against heartwater. These responses are mediated by CD8+ and CD4+T lymphocytes through the production of the Th1 cytokine, IFN-γ. A successful heartwater DNA vaccine might result from immunogens that can elicit similar immune responses. T cell epitopes, the minimal antigenic units of the whole pathogen protein, are presented by major histocompatibility complex (MHC) molecules that are recognised by the host T lymphocytes. Although these small sequences can induce protective immune responses, some can inhibit such responses or induce immunopathology. Selecting only T cell epitopes that induce protective immune responses for incorporation into a multi-epitope DNA vaccine could result in an effective vaccine.

The Applicant has identified 17 CD4+ T cell and CD8+ cytotoxic T lymphocyte (CTL) epitopes from the following *E. ruminantium* antigens: Erum0660; Erum5420; Erum1150; Erum7360; Erum7140; Erum7350; Erum7620; Erum8010; Erum7320 and Erum2540. Epitopes were identified in vitro using immune sheep PBMC wherein, five of these epitopes induced positive CTL responses, proliferation of CD8+ T cells as well as production of IFN-γ by these cells and expression of cytokines like IL-18 and TNF-α. Twelve of these epitopes were shown to specifically induce IFN-γ production by memory CD4+ and CD8+ T cells in addition to expression of cytokines like IL-12, TGF, iNOS, IL-2, IL-1a, TNF-α and GM-CSF.

These epitopes were used to construct different multi-epitope DNA vaccines. Multi-epitope DNA vaccines have been constructed and showed effective efficiencies against several pathogens like *M. tuberculosis, Eimeria tenelle, Toxoplasma gondii*.

The innate immune system recognises specific molecular structures present in the pathogen in order to activate the adaptive immunity. As subunit vaccines, DNA vaccines lack these molecular structures found in live organisms or attenuated vaccines. Hence, they are often unable to stimulate pathogen-specific adaptive immune responses and have to rely on the incorporation of effective adjuvants to enhance their immunogenicity.

Adjuvants, such as Monophosphoryl lipid A (MPL), can function either as immunostimulants which activate innate immune pathways and aid in the enhancement of adaptive immune responses or as vehicles for antigen delivery (e.g. microparticles) which improve delivery of vaccines to the immune system. MPL adjuvant, a derivative of lipopolysaccharide (LPS) activates Toll-like receptor 4 (TLR4) which is one of the innate receptors resulting in activation of multiple innate functions that will support activation of adaptive immune responses. Microparticles can be used to adsorb or encapsulate DNA vaccines in biodegradable particles such as Poly Lactic-co-Glycolic Acid (PLGA). PLGA microparticles have been reported to improve delivery of DNA to antigen presenting cells (APC), enhance gene expression and to protect the DNA against nuclease degradation. Additionally, PLGA microparticles can be formulated for sustained release of DNA over a prolonged period often resulting in improved duration of vaccine induced immunity.

SUMMARY OF THE INVENTION

According to a first aspect of the invention there is provided for a nucleic acid comprising at least one sequence encoding an *Ehrlichia ruminantium* antigenic epitope which induces a CD4 immune response selected from the group consisting of SEQ ID NOs:55-61 and SEQ ID NOs:66-70; at least one sequence encoding an *Ehrlichia ruminantium* antigenic epitope which induces a CD8 immune response selected from the group consisting of SEQ ID NOs:62-65 and SEQ ID NO:71; an internal ribosomal sequence; and a ubiquitin signal.

Preferably, the nucleic acid of the invention comprises a sequence encoding *Ehrlichia ruminantium* antigenic epitopes which induce a CD4 immune response having amino acid sequences of SEQ ID NOs:9-16; a sequence encoding *Ehrlichia ruminantium* antigenic epitopes which induce a CD8 immune response having amino acid sequences of SEQ ID NOs:17-19 and 72; an internal ribosomal sequence; and a ubiquitin signal.

In one embodiment of invention the nucleic acid further comprises a sequence encoding *Ehrlichia ruminantium* antigenic epitopes which induce a CD4 immune response having amino acid sequences of SEQ ID NOs:20-24 and a sequence encoding *Ehrlichia ruminantium* antigenic epitopes which induce a CD8 immune response having an amino acid sequence of SEQ ID NO:25.

In a second embodiment the nucleic acid may further comprise a sequence encoding a CpG motif, may optionally further comprise a sequence encoding an MHC II targeting peptide, and/or may further comprise a sequence encoding a sheep CXCL1 signal peptide. The nucleic acid of the present invention may also optionally further comprise a sequence encoding an IL-3 sheep signal peptide, may optionally further comprise a sequence encoding a KFERQ peptide sequence (SEQ ID NO:40), may optionally further comprise a sequence encoding an Ig Kappa signal peptide, and/or may further comprise a sequence encoding a His tag.

In a third embodiment the nucleic acid may be operably linked to a promoter sequence, and may be optionally linked to other regulatory sequences that allow for transcription of a protein encoded by the nucleic acid in a cell, preferably an animal cell.

In a second aspect of the present invention there is provided for a multi-epitope DNA vaccine comprising a nucleic acid as described herein. In one embodiment the multi-epitope DNA vaccine includes a pharmaceutically acceptable diluent, excipient or adjuvant, preferably a pharmaceutically acceptable adjuvant, most preferably monophosphoryl lipid A.

According to a further embodiment a polypeptide expressed from the multi-epitope DNA vaccine is capable of eliciting a protective immune response against heartwater disease.

In a third aspect of the present invention there is provided for a polypeptide encoded by a nucleic acid described herein. The polypeptide may be selected from the group consisting of SEQ ID NO:1 to 4.

According to a fourth aspect of the present invention there is provided for a nucleic acid described herein, a multi-epitope DNA vaccine described herein, or a polypeptide described herein, for use in a method of inducing an immune response against heartwater disease in a subject, the method comprising administering a therapeutically effective amount of the nucleic acid, DNA vaccine or the polypeptide to the subject. It will be appreciated that in a preferred embodiment of the invention the subject is a mammal, preferably a mammal selected from the group consisting of cattle, sheep, goats, antelope, and buffalo.

In a further aspect of the invention there is provided for the use of a nucleic acid described herein, or a polypeptide described herein, in the manufacture of a vaccine for use in a method of inducing an immune response against heartwater disease in a subject, the method comprising administering a therapeutically effective amount of the vaccine to the subject. It will be appreciated that in a preferred embodiment of the invention the subject is a mammal, preferably a mammal selected from the group consisting of cattle, sheep, goats, antelope, and buffalo.

In yet another aspect of the invention there is provided for a method of inducing an immune response against heartwater disease in a subject, the method comprising administering a therapeutically effective amount of a nucleic acid described herein, a multi-epitope DNA vaccine described herein, or a polypeptide described herein, to the subject.

It will be appreciated that in a preferred embodiment of the invention the subject is a mammal, preferably a mammal selected from the group consisting of cattle, sheep, goats, antelope, and buffalo.

BRIEF DESCRIPTION OF THE DRAWINGS

Non-limiting embodiments of the invention will now be described by way of example only and with reference to the following figures:

FIG. 2: DNA sequence of total codon optimised pLamp vaccine construct.

FIG. 3: DNA sequence of total codon optimised pME1 vaccine construct.

DETAILED DESCRIPTION OF THE PREFERRED EMBODIMENT

Figure 1:
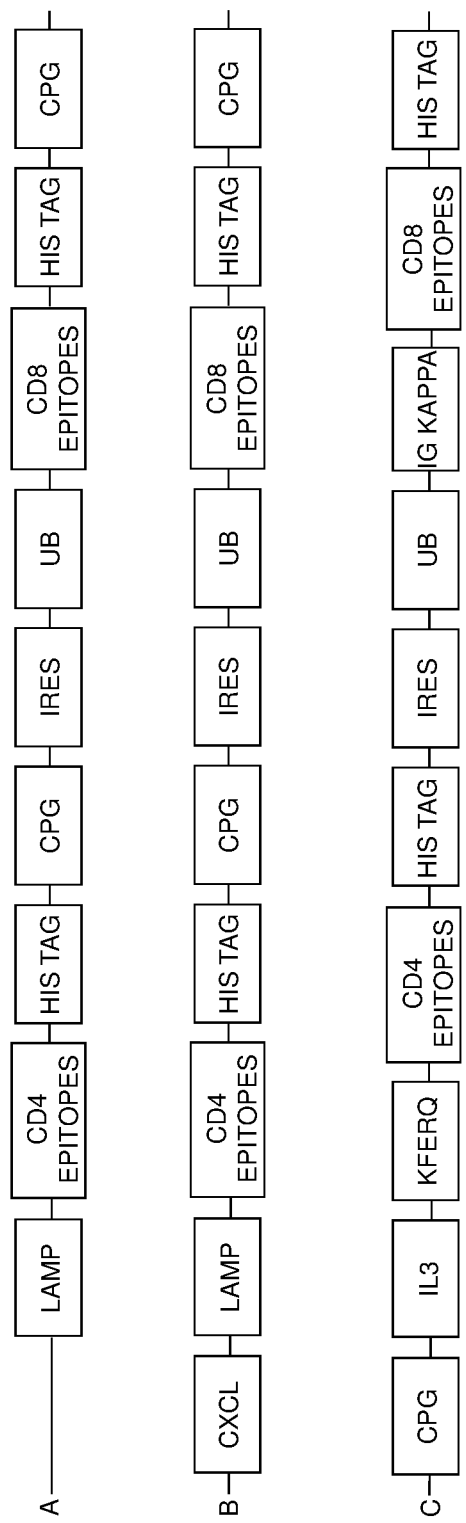
FIG. 1: Schematic representation of the three constructs used in the study. A represents pSignal plus, B represents pLamp, C represents pME1. CD4 epitope sequences had GPGPG spacers between them while CD8 epitope sequences had AYY spacers.

Previously, a heartwater experimental DNA vaccine was successful in the laboratory but failed in the field. Multi-epitope DNA vaccines could provide a better alternative since they can incorporate both CD4+ and CD8+ cytotoxic T lymphocyte (CTL) epitopes. The Applicant has investigated the use of multi-epitope DNA vaccines against heartwater challenge in sheep using *Ehrlichia ruminantium* infected ticks. All the experimental animals were immunised via the intramuscular (IM) route as well as intradermal route using a gene gun.

The multi-epitope DNA vaccine constructs were tested in the presence of the adjuvant Monophosphoryl Lipid A (MPL) which was either applied topically to the gene gun inoculation site or co-administered with the vaccine via intramuscular (IM) route. Initially two constructs (namely, pSignal plus and pLamp) were tested with MPL applied topically. It was observed that in this formulation the constructs failed to protect any of the challenged sheep. However, when the pLamp construct was co-administered with MPL via IM route, this improved the protective efficiency of this construct. In this formulation the construct, protected three of the five sheep against tick challenge. Two more multi-epitope DNA constructs were tested, namely, pME1 and pME2 with the adjuvant co-administered with the vaccine via IM route. pME1 failed to protect any of the challenged sheep while pME2 protected one of the five sheep against tick challenge. Additionally, pME2 was adsorbed onto Poly Lactic-co-Glycolic Acid (PLGA) biodegradable microparticles and co-administered subcutaneous with the adjuvant. In this formulation pME2 protected two of the five tick challenged sheep. However, the control construct in this formulation also protected one of the five tick-challenged sheep.

Cellular immune response evaluations both before and after challenge varied amongst the different animals which could have been due to their different genetic background. For the first time in a heartwater DNA vaccine trial, laboratory *E. ruminantium* infected ticks were used to challenge sheep and a multi-epitope DNA vaccine construct co-administered with MPL adjuvant provided protection.

The Applicant constructed four multi epitope DNA vaccines and their efficacy was tested in sheep against heartwater challenge using *E. ruminantium* infected ticks. The DNA vaccines were administered in the presence of MPL adjuvant which was given topically or co-administered with the DNA vaccine via intramuscular (IM) injection. Additionally, one of the constructs was adsorbed onto PLGA microparticles and delivered subcutaneously (SC). Cellular immune responses induced after immunisation and challenge were also studied.

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

By "heartwater" is meant a tick-borne rickettsial disease of domestic and wild ruminants. It is caused by *Ehrlichia ruminantium* (formerly *Cowdria ruminantium*) an intracellular gram-negative coccal bacterium (also referred to as *Rickettsia ruminantium*). The disease is spread by bont ticks, which are members of the genus *Amblyomma*. Affected mammals include cattle, sheep, goats, antelope, and buffalo. Heartwater disease may also be referred to as "cowdriosis", "nintas" and "ehrlichiosis".

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

An "antigen" is a compound, composition, or substance that can stimulate the production of antibodies and/or a CD4+ or CD8+ T cell response in an animal, including compositions that are injected or absorbed into an animal. An antigen reacts with the products of specific humoral or cellular immunity, including those induced by heterologous immunogens. The term "antigen" includes all related antigenic epitopes. An "epitope" refers to a site on an antigen, including chemical groups or peptide sequences on a molecule that are antigenic, i.e. that elicit a specific immune response. An antibody specifically binds a particular antigenic epitope on a polypeptide. Accordingly, "multiepitope" refers to a molecule or polypeptide comprising more than one epitope or a site which is antigenic for more than one antibody.

The terms "nucleic acid" or "nucleic acid molecule" encompass both ribonucleotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides. By "cDNA" is meant a complementary or copy DNA produced from an RNA template by the action of RNA-dependent DNA polymerase (reverse transcriptase).

Accordingly, a "cDNA clone" refers to a duplex DNA sequence which is complementary to an RNA molecule of interest, and which is carried in a cloning vector. The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of the expressed fusion protein or of the polypeptide encoded by the nucleic acid molecule. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or 100% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

In some embodiments, the nucleic acid molecules of the invention may be operably linked to other sequences. By "operably linked" is meant that the nucleic acid molecules of the invention and regulatory sequences are connected in such a way as to permit expression of the antigens when the appropriate molecules are bound to the regulatory sequences.

The term "recombinant" means that something has been recombined. When used with reference to a nucleic acid construct the term refers to a molecule that comprises nucleic acid sequences that are joined together or produced by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention.

The term "vector" refers to a means by which polynucleotides or gene sequences can be introduced into a cell. There are various types of vectors known in the art including plasmids, viruses, bacteriophages and cosmids. Generally, polynucleotides or gene sequences are introduced into a vector by means of a cassette. The term "cassette" refers to a polynucleotide or gene sequence that is expressed from a vector. A cassette generally comprises a gene sequence inserted into a vector, which in some embodiments, provides regulatory sequences for expressing the polynucleotide or gene sequences. In other embodiments, the vector provides the regulatory sequences for the expression of the DNA vaccine in a host cell. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

The DNA vaccine or compositions of the invention can be provided either alone or in combination with other compounds (for example, nucleic acid molecules, small molecules, peptides, or peptide analogues), in the presence of a liposome, an adjuvant, or any carrier, such as a pharmaceutically acceptable carrier and in a form suitable for administration to mammals, for example, cattle, sheep, goats, antelope, and buffalo etc.

As used herein a "pharmaceutically acceptable carrier" or "excipient" includes any and all antibacterial and antifungal agents, coatings, dispersion media, solvents, isotonic and absorption delaying agents, and the like that are physiologically compatible. A "pharmaceutically acceptable carrier" may include a solid or liquid filler, diluent or encapsulating substance which may be safely used for the administration of the fusion protein or vaccine composition to a subject. The pharmaceutically acceptable carrier can be suitable for intramuscular, intraperitoneal, intravenous, oral or sublingual administration. Pharmaceutically acceptable carriers include sterile aqueous solutions, dispersions and sterile powders for the preparation of sterile solutions. The use of media and agents for the preparation of pharmaceutically active substances is well known in the art. Where any conventional media or agent is incompatible with the active compound, use thereof in the pharmaceutical compositions of the invention is not contemplated. Supplementary active compounds can also be incorporated into the compositions.

Suitable formulations or compositions to administer the DNA vaccine and compositions of the present invention to subjects for example, cattle, sheep, etc. fall within the scope of the invention. Any appropriate route of administration may be employed, such as, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, topical, or oral administration.

As used herein the term "subject" includes both wild and domestic ruminants.

For vaccine formulations, an effective amount of the DNA vaccine or compositions of the invention can be provided, either alone or in combination with other compounds, with immunological adjuvants, for example, Monophosphoryl lipid A (MPL), aluminium hydroxide dimethyldioctadecylammonium hydroxide or Freund's incomplete adjuvant. The DNA vaccine or compositions of the invention may also be linked with suitable carriers and/or other molecules, in order to enhance immunogenicity. Further microparticles can be used to adsorb or encapsulate the DNA vaccine or compositions of the present invention in biodegradable particles such as Poly Lactic-co-Glycolic Acid (PLGA).

In some embodiments, the DNA vaccine or compositions according to the invention may be provided in a kit, optionally with a carrier and/or an adjuvant, together with instructions for use.

The term "adjuvant" as used herein refers to substances that have immunopotentiating effects and are added to or co-formulated with an active agent in order to enhance, induce, elicit, and/or modulate the immunological response against the active agent when administered to a subject. Adjuvant compositions of the present invention include oil emulsions (Freund's adjuvant), oil based compounds (e.g. MF59, ISA51, ISA720), saponins, aluminium or calcium salts (i.e. Alum), non-ionic block polymer surfactants, lipopolysaccharides (LPS), attenuated or killed mycobacteria, tetanus toxoid, monophosphoryl lipid A, imiquimod, resiquimod, polyI:C, CpG containing oligonucleotides, lipoproteins and others. Many adjuvants produce undesirable side effects in humans such as inflammation at the site of injection, these side effects can limit their use and efficacy, and thus there is a need for alternative, and improved, adjuvants. Preferably the adjuvant is monophosphoryl lipid A.

An "effective amount" of a compound according to the invention includes an immunologically effective amount, or a prophylactically effective amount. A therapeutically effective amount of a compound may vary according to factors such as the disease state, age, sex, and weight of the individual, and the ability of the compound to elicit a desired response in the subject, including, for example, cattle, sheep, goats, antelope, and buffalo etc. Dosage regimens may be adjusted to provide the optimum therapeutic response. An effective amount is also one in which any toxic or detrimental effects of the compound are outweighed by the immunologically or prophylactically beneficial effects.

The dosage of the DNA vaccine or compositions of the present invention will vary depending on the symptoms, age and body weight of the subject, the nature and severity of the disorder to be prevented, the route of administration, and the form of the composition. Any of the compositions of the invention may be administered in a single dose or in multiple doses. The dosages of the compositions of the invention may be readily determined by techniques known to those of skill in the art or as taught herein.

By "immunogenically effective amount" is meant an amount effective, at dosages and for periods of time necessary, to achieve a desired immune response, including a cellular and/or humoral response. The desired immune response may include stimulation or elicitation of an immune response, for instance a T cell response.

A "prophylactically effective amount" refers to an amount effective, at dosages and for periods of time necessary, to achieve a desired prophylactic result, such as prevention of onset of a heartwater disease. Typically, a prophylactic dose is used in subjects prior to or at an earlier stage of disease, so that a prophylactically effective amount may be less than a therapeutically effective amount.

Dosage values may vary for any particular subject and specific dosage regimens may be adjusted over time according to the individual need and the judgment of the person administering or supervising the administration of the DNA vaccine or compositions of the invention. Dosage ranges set forth herein are exemplary only and do not limit the dosage ranges that may be selected. The amount of active compound(s) in the composition may vary according to factors such as the disease state, age, sex, and weight of the individual. Dosage regimens may be adjusted to provide the optimum response. For example, a single dose may be administered, or multiple doses may be administered over time. It may be advantageous to formulate the compositions in dosage unit forms for ease of administration and uniformity of dosage.

The term "preventing", when used in relation to an infectious disease, or other medical disease or condition, is well understood in the art, and includes administration of a composition which reduces the frequency of or delays the onset of symptoms of a condition in a subject relative to a subject which does not receive the composition. Prevention of a disease includes, for example, reducing the number of diagnoses of the infection in a treated population versus an untreated control population, and/or delaying the onset of symptoms of the infection in a treated population versus an untreated control population.

The term "prophylactic or therapeutic" treatment is well known to those of skill in the art and includes administration to a subject of one or more of the DNA vaccines or compositions of the invention. If the composition is administered prior to clinical manifestation of the unwanted condition (e.g., disease or other unwanted state of the subject) then the treatment is prophylactic.

Toxicity and therapeutic efficacy of compositions of the invention may be determined by standard pharmaceutical procedures in cell culture or using experimental animals, such as by determining the $LD_{50}$ and the $ED_{50}$. Data obtained from the cell cultures and/or animal studies may be used to formulating a dosage range for use in a subject. The dosage of any composition of the invention lies preferably within a range of circulating concentrations that include the $ED_{50}$ but which has little or no toxicity. The dosage may vary within this range depending upon the dosage form employed and the route of administration utilized.

The following examples are offered by way of illustration and not by way of limitation.

Example 1

Construction of the Multi-Epitope DNA Vaccines

Four DNA constructs, designated pSignal plus (SEQ ID NO:5), pLamp (SEQ ID NO:6), pME1 (SEQ ID NO:7) and pME2 (SEQ ID NO:8) containing codon optimised nucleotide sequences encoding E. ruminantium CD4 and CD8 peptides (Table 1) were designed and synthesised (FIG. 1).

The first construct, pSignal plus (SEQ ID NO:5) contained sheep CXCL1 signal sequence (SEQ ID NO:29) encoding a CXCL1 signal peptide (SEQ ID NO:30) followed by a MHC II targeting sequence (LAMP sequence of SEQ ID NO:31 encoding a peptide of SEQ ID NO:32). This was followed by eight codon optimised nucleotide sequences (SEQ ID NOs:55-62) encoding eight CD4 epitopes (SEQ ID NOs:9-16) that contained sequences (selected from SEQ ID NOs:46-51) encoding GPGPG spacers (SEQ ID NO:45) in between, that disrupt possible junctional CD4 epitopes and optimise processing. The codon optimised nucleotide sequence of the CD4 epitopes, including spacers, used in the pSignal plus construct is provided as SEQ ID NO:26. The pSignal plus construct further contained a CpG motif (CpG2135) (SEQ ID NO:33) to activate the innate immune response. This was followed by an internal ribosomal sequence (IRES) of SEQ ID NO:34 that allows for separation of CD4 and CD8 epitopes. A nucleotide sequence (SEQ ID NO:35) encoding an Ubiquitin (UB) signal (SEQ ID NO:36) for degradation via the proteosome was added before the four codon optimised nucleotide sequences (SEQ ID NOs:63-65 and SEQ ID NO:73) encoding four CD8 epitopes (SEQ ID NOs:17-19 and SEQ ID NO:72) that contained a nucleotide sequence encoding AYY spacers (selected from SEQ ID NOs:52-53) between them. The codon optimised nucleotide sequence of the CD8 epitopes, including spacers, used in the pSignal plus construct is provided as SEQ ID NO:27. A second CpG motif (SEQ ID NO:33) followed at the end (FIG. 1A). The pSignal plus construct further included a nucleotide sequence (SEQ ID NO:43) encoding a His tag (SEQ ID NO:44) for protein purification.

The second construct, pLamp (SEQ ID NO:6; FIG. 2) was exactly the same as pSignal plus except that it did not contain the CXCL1 signal sequence (FIG. 1B). The synthetic construct (GeneScript) was cloned into the NotI/XbaI restriction site of the pCDNA3.1(+) vector to generate the pSignal plus and pLamp constructs.

An additional two multiepitope DNA vaccines were constructed. The third construct, designated pME1 (SEQ ID NO:7; FIG. 3) included six codon optimised nucleotides sequences (SEQ ID NOs:66-71) encoding 6 new epitopes (SEQ ID NOs:20-25). The codon optimised nucleotide sequence of the epitopes, including spacers, used in the pME1 construct is provided as SEQ ID NO:28. The pME1 construct further contained the CpG motif (SEQ ID NO:33), a nucleotide sequence (SEQ ID NO:37) encoding an IL-3 sheep signal sequence (SEQ ID NO:38) to target proteins to endoplasmic reticulum for secretion and uptake by antigen presenting cells, for MHC class II presentation. The pME1 construct also included a nucleotide sequence (SEQ ID NO:39) encoding a KFERQ peptide sequence targeting CD4 peptides to lysosome (SEQ ID NO:40) for processing. This was followed by five CD4 epitopes (SEQ ID NOs:20-24) with GPGPG spacers (SEQ ID NO:45) encoded by a nucleotide sequence of SEQ ID NO:54 in between. The pME1 construct included an IRES sequence (SEQ ID NO:34) and a nucleotide sequence of SEQ ID NO:35 encoding an UB signal of SEQ ID NO:36. The pME1 construct further included a nucleotide sequence (SEQ ID NO:41) encoding an Ig Kappa signal peptide (SEQ ID NO:42) that facilitates CD8 peptide transport to ER and one CD8 epitope (SEQ ID NO:25) followed by a nucleotide sequence (SEQ ID NO:43) encoding a His tag (SEQ ID NO:44) for protein purification (FIG. 1C).

The fourth construct, pME2 (SEQ ID NO:8), was exactly the same as pME1 but it contained the six epitopes from the pME1 construct plus the 11 epitopes used in pSignal and pLamp.

These plasmids were transformed into *E. coli* and cloning was confirmed by DNA sequencing. For immunisation, plasmid DNA was prepared using the Endofree® Plasmid Maxi Kit (Qiagen) following the manufacturer's instructions. After digestion with appropriate restriction enzyme, the integrity of the plasmid DNA was checked by agarose gel electrophoresis. The DNA concentration and purity was determined using a spectrophotometer ND-1000 Nanodrop® (Thermo Scientific). The plasmid DNA was adjusted to a final concentration of 1 µg/ml in PBS and stored at −20° C. until use.

Example 2

Preparation of pDNA for Gene Gun Inoculations
Precipitation of pDNA onto Gold Particles The plasmids were precipitated onto 1.6 µm gold particles before each inoculation. The manufacturer's instructions were closely followed in coating DNA to gold particles and operating the gene gun. Twenty-five mg of gold particles of 1.6 µm of diameter (BioRad) was suspended in 250 µl solution of 0.05 M spermidine (Sigma). 250 µg of DNA solution was added into gold/spermidine and precipitated on gold by adding drop wisely 250 µl of 1 M $CaCl_2$ under continuous vortexing. The mixture was incubated at room temperature for 10 min, followed by three washes with 100% ethanol, and finally resuspended in 0.1 mg PVP (BioRad) at the final volume of 3 ml.

Preparation of Gold-Coat Tubing

Before coating, the tubing was dried in the gene gun tubing prep station (BioRad) with nitrogen gas (0.4 pressure) for a minimum of 20 minutes. The solution was then introduced into the dry polypropylene tubing, placed in the tubing prep station where gold settled for 3-5 min. Ethanol/PVP was removed, and the tubing continuously rotated to spread the gold/DNA precipitated uniformly. Lastly, the cartridge preparation was dried with nitrogen flow for 5-10 min. The tubing was removed and cartridges were cut using a tubing-cutter. One preparation contained approximately 50 cartridges which were kept dry in a cartridge storage vial with desiccant pellets. One cartridge contained 5 µg of plasmid DNA precipitated on 0.5 mg gold.

Adsorption of pDNA onto Microparticles and the Adsorption Efficiency of the Microparticles The pDNA construct was adsorbed onto PLGA 502H polymer (Sigma) as described in Tshikhudu et al., 2010. Briefly, 200 mg of polymer was dissolved in 10 ml dichloromethane (DCM) and sonicated in Tris EDTA (TE) buffer using the Branson Sonifier® at 50 Watts and 20 pulse cycle. The primary emulsion was added to 50 ml of 0.5% cetyltrimethylammonium bromide (CTAB) solution. The solution was homogenised for 60 sec at 6000 rpm using the Ultra Turrax homogeniser and added to another 50 ml of 0.5% CTAB. The secondary emulsion was stirred overnight in an open beaker to remove the solvent. The hardened microparticles were collected by centrifugation at 13,000×g for 10 min and freeze dried overnight. The dried particles (100 mg) were incubated with 500 µg of pDNA in 1 ml TE buffer for 6 h at 4° C. on a platform shaker. Particles were collected by centrifugation and freeze dried. The supernatant was used for determining the amount of pDNA that was adsorbed onto the particles. Absorbance at 260 nm (A260 nm) was measured using a spectrophotometer ND-1000 Nanodrop® (Thermo Scientific). Particle size and surface morphology were determined by scanning electron microscope (SEM).

Characterisation of the Microparticles Adsorbing pDNA

Figure 4:
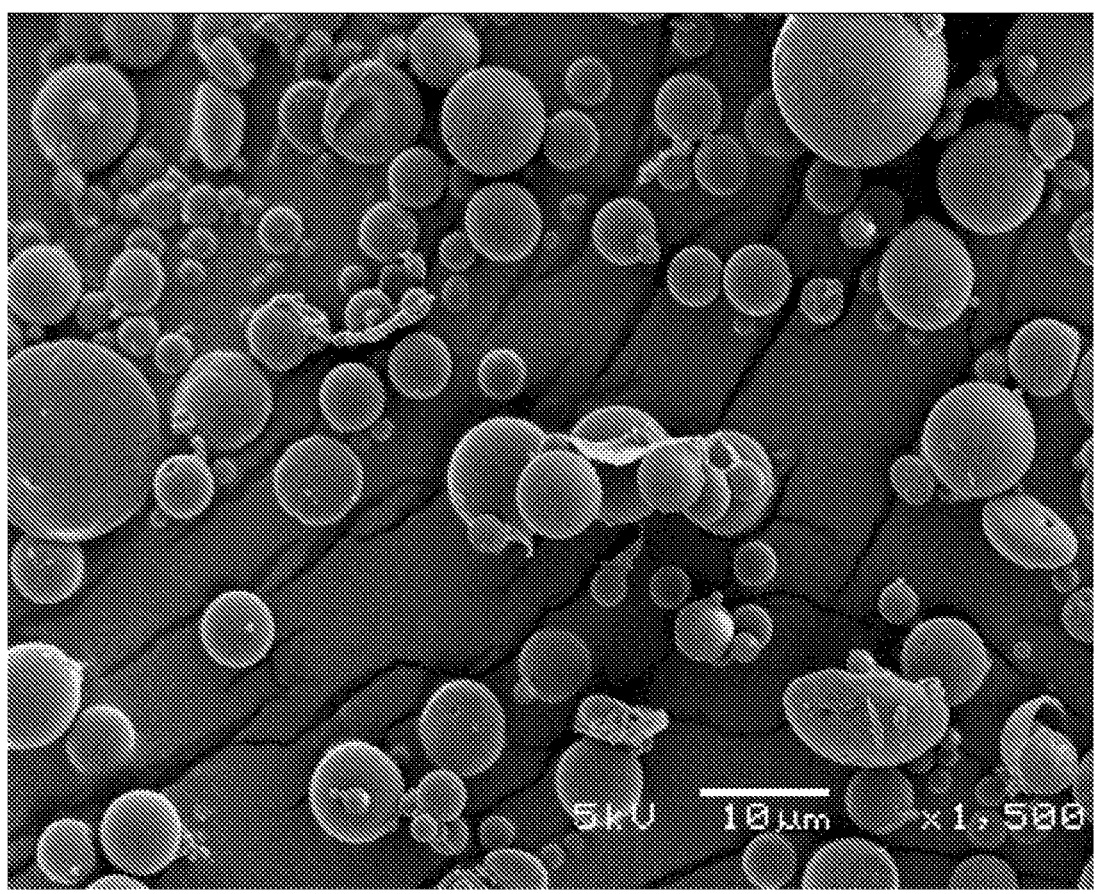
FIG. 4: Scanning electron micrograph of PLGA microparticles adsorbing pDNA.

The morphology of the prepared microparticles was studied using a scanning electron microscope (FIG. 4). The PLGA microparticles adsorbing the plasmid DNA had smooth, spherical and non-porous surfaces with diameters of 5.0 µm-20 µm. The adsorption efficiency for these particles was between 81% and 94% adsorbing approximately 4 µg of plasmid DNA per 1 mg of the polymer.

Example 3

MHC Typing of the Experimental Animals

Whole blood from each sheep was collected in BD Vacutainer K2E tubes (BD Biosciences) containing EDTA. Samples of genomic DNA were obtained from whole blood

TABLE 1

Amino acid sequences of the peptides selected for inclusion in the multi-epitope DNA vaccines

| pSignal plus and pLamp | pLamp-1 (ME1) | pLamp-2 (ME2) |
|---|---|---|
| Erum7140-p6 (SEQ ID NO: 9) | Erum0660-p42 (SEQ ID NO: 20) | Combination of peptides in pLamp and pLamp-1 |
| Erum7140-p7 (SEQ ID NO: 10) | Erum5420-p13 (SEQ ID NO: 21) | (SEQ ID NOs: 9-25) |
| Erum7140-p20 (SEQ ID NO: 11) | Erum5420-p14 (SEQ ID NO: 22) | |
| Erum7350-p9 (SEQ ID NO: 12) | Erum1150-p18 (SEQ ID NO: 23) | |
| Erum7620-p12 (SEQ ID NO: 13) | Erum1150-p19 (SEQ ID NO: 24) | |
| Erum8010-p8 (SEQ ID NO: 14) | Erum7360-p8 (SEQ ID NO: 25) | |
| Erum7320-p21 (SEQ ID NO: 15) | | |
| Erum2540-p21 (SEQ ID NO: 16) | | |
| Erum2540-p6 (SEQ ID NO: 17) | | |
| Erum2540-p16 (SEQ ID NO: 18) | | |
| Erum2540-p19 (SEQ ID NO: 19) | | |
| Erum2540-p20 (SEQ ID NO: 72) | | | and purified using the Generation@ Capture Column Kit (Gentra systems) according to the instructions of the manufacture. Typing for Ovine MHC Ovar-DRB1 was performed using polymerase chain reaction-restriction fragment length polymorphism (PCR-RFLP) as described by Konnai et al., 2003. Briefly, the second exon of Ovar-DRB1 was amplified by nested PCR using different primers. The resulting nested PCR product was digested overnight at 37° C. with 5 U of RsaI, HaeIII, PsuI, SacI, SacII, DdeI, NciI, HinII, EcoRI or at 60° C. with 5 U of BstNI. Samples were resolved by agarose gel electrophoresis and the resulting restriction patterns were compared to published restriction maps (Konnai et al., 2003).

In order to see if the selected epitopes are MCH restricted, we performed MHC typing for all our experimental animals. PCR-RFLP was used to analyse the polymorphism of the ovine MHC complex class II DRB1 second exon (Ovar-DRB1). For sheep in animal trial 1 (Table 2), the results showed that sheep 3321, 3315 and 3318 had a common allele *03411 while sheep 3300, 3338 and 3314 also shared a common allele *0201. Two different alleles (*0323 and *0333) were obtained for sheep 3304, 3335 and 3323. Sheep 3295, 3297 and 3303 shared a similar unknown1 allele while 3327, 3328 and 3329 also shared another common unknown2 allele. In animal trial 2 (Table 3), sheep 3499, 3320, 3493, 3488, 3482 and 3491 shared a common allele *0203. The first set of two different alleles which was *0323

TABLE 2

MHC typing of sheep in animal trial 1 and summary of the survival of immunised sheep following tick challenge.

| Treatment | Sheep number | MHC DRB1 alleles | Days to temperature above 40° C. | Highest temperature reached (° C.) | Survival (S) or treatment (T) or dead (D) on day shown |
|---|---|---|---|---|---|
| Empty vector | 3313 | | 14 | 42.0 | T (19) |
| | 3310 | | 14 | 41.8 | T (17) |
| | 3311 | | 16 | 42.0 | T (21) |
| | 3331 | | 14 | 41.9 | D (20) |
| | 3330 | | 16 | 40.1 | T (19) |
| Empty vector + adjuvant | 3295 | | 16 | 42.0 | T (20) |
| | 3321 | *03411 | 19 | 41.5 | T (22) |
| | 3304 | *0323; *0333 | 19 | 42.0 | D (21) |
| | 3329 | Unknown2 | 16 | 42.0 | T (20) |
| | 3300 | *0201 | 23 | 41.6 | T (23) |
| pLamp + adjuvant | 3297 | Unknown 1 | 15 | 42.0 | T (19) |
| | 3315 | *03411 | 18 | 41.8 | T (20) |
| | 3335 | *0323; *0333 | 16 | 42.0 | T (19) |
| | 3328 | Unknown2 | 14 | 42.0 | T (18) |
| | 3338 | *0201 | 20 | 41.9 | T (21) |
| pSignal plus + adjuvant | 3303 | Unknown1 | 19 | 41.7 | T (21) |
| | 3318 | *03411 | 17 | 42.0 | T (20) |
| | 3323 | *0323; *0333 | 20 | 41.5 | T |
| | 3327 | Unknown2 | 16 | 42.0 | T (19) |
| | 3314 | *0201 | 17 | 41.0 | T (22) |
| Naive | 3308 | | 19 | 42.0 | T (22) |
| | 3317 | | 15 | 42.0 | T (18) |
| Positive control | 3291 | | — | 39.6 | S |
| | 3292 | | — | 39.8 | S |

TABLE 3

MHC typing of sheep in animal trial 2 and summary of the survival of immunised sheep following tick challenge.

| Treatment | Sheep number | MHC DRB1 alleles | Days to temperature above 40 (° C.) | Highest temperature reached (° C.) | Survival (S) or treatment (T) or dead (D) on day shown |
|---|---|---|---|---|---|
| Empty vector co-administered with adjuvant | 3499 | *0203 | 18 | 41.9 | T (20) |
| | 3320 | *0203 | 20 | 41.0 | T (21) |
| Adsorbed Empty vector co-administered with adjuvant | 3489 | *0323; *0333 | 28 | 42.0 | T (29) |
| | 3493 | *0203 | 18 | 42.0 | T (27) |
| | 3483 | | 25 | 41.8 | T (27) |
| | 3484 | *0702; *0703 | — | 39.6 | S |
| | 3490 | Unknown5 | 16 | 42.0 | T (18) |
| pLamp co-administered with adjuvant | 3299 | | 16 | 42.0 | T (20) |
| | 3488 | *0203 | — | 39.3 | S |
| | 3333 | Unknown4 | 16 | 41.8 | T (20) |
| | 3498 | *0702; *0703 and Unknown3 | — | 39.6 | S |
| | 3337 | Unknown5 | — | 39.0 | S |
| pME1 co-administered with adjuvant | 3302 | *0332 | 17 | 42.0 | T (20) |
| | 3322 | *0201 | 18 | 41.4 | D (21) |
| | 3325 | Unknown4 | 16 | 42.0 | T (16) |
| | 3494 | *0702; *0703 | 29 | 41.6 | T (31) |
| | 3293 | | 16 | 41.4 | T (20) |

TABLE 3-continued

MHC typing of sheep in animal trial 2 and summary of the survival of immunised sheep following tick challenge.

| Treatment | Sheep number | MHC DRB1 alleles | Days to temperature above 40 (° C.) | Highest temperature reached (° C.) | Survival (S) or treatment (T) or dead (D) on day shown |
|---|---|---|---|---|---|
| pME2 co-administered with adjuvant | 3309 | *0323; *0333 | 17 | 42.0 | T (20) |
| | 3482 | *0203 | 16 | 42.0 | T (18) |
| | 3332 | Unknown4 | — | 39.4 | S |
| | 3495 | *0702; *0703 | 18 | 41.8 | T (20) |
| | 3324 | | 16 | 41.5 | T (21) |
| Adsorbed pME2 co-administered with adjuvant | 3487 | *0323; *0333 | 28 | 41.6 | T (29) |
| | 3491 | *0203 | — | 39.3 | S |
| | 3316 | *0801 | — | 39.3 | S |
| | 3501 | *0702; *0703 and Unknown3 | 17 | 42.0 | T (18) |
| | 3485 | Unknown5 | 25 | 40.9 | D (27) | and *0333 was obtained with sheep 3489, 3309 and 3487. The second set of two different alleles (*0702 and *0703) was obtained for sheep 3484, 3498, 3494, 3495 and 3501.

Additionally, sheep 3498 and 3501 shared a third common new/unknown3 allele. Sheep 3333, 3325 and 3332 shared a common new/unknown4 allele while sheep 3337, 3485 and 3490 also shared another common new/unknown5 allele. Allele *0801 and *0201 were obtained for sheep 3316 and 3322 respectively. From the MHC typing results, animals were divided amongst the experimental groups in such a way that each MHC type is represented in each group.

Example 4

Immunisation and Challenge of Animals

Animals

Merino sheep aged between 8 and 12 months were obtained from heartwater free regions in South Africa and tested negative for heartwater using the pCS20 qPCR (Steyn et al., 2008). All animal research protocols were approved by the animal ethics committee at the ARC-OVI. Approval was also obtained by the South African department of agriculture, forestry and fisheries (DAFF).

Animal Trial 1

In trial 1, the adjuvant was applied topically to the gene gun inoculation site. Groups of sheep (n=5) were immunised three times in three weeks' interval with the empty vector (pCDNA3.1(+) vector) or different multi epitope DNA vaccine constructs (Table 4): 1. Empty vector, 2. Empty vector+adjuvant, 3. pLamp+adjuvant, 4. pSignal Plus+adjuvant. All the sheep received 200 µg pDNA delivered by IM injection (Pretorius et al., 2007) and 50 µg pDNA delivered intra dermal (ID) by the gene gun using the Helios Gene Gun™ system (BioRad) with Helium pressure of 300 psi. The sheep that received the adjuvant, had 20 µl of MPL applied topically to surface of their shaved ears prior to gene gun inoculations. Additional control groups were the non-immunised naïve sheep (n=2) and the positive control (n=2) which were tick infected with E. ruminantium Welgevonden strain as described previously (Mahan et al., 1998) and treated with Terramycin®100 (1 ml/10 kg) on the third day of febrile reaction. Five weeks after the third DNA inoculation, all the sheep were tick challenged with E. ruminantium infected adult ticks. Briefly, an area on the back of each sheep was shaved and a bag was attached to the shaven area. Five E. ruminantium infected male ticks were added to the bag and allowed to feed for at least three days. After this, five E. ruminantium infected female ticks were also added to the bag and allowed to feed for 6 days or until engorged. The sheep were monitored for the onset clinical symptoms and rectal temperatures were measured daily. To determine the severity of infection, clinical signs were scored using a reaction index (RI) as described by Pretorius et al., 2007. Animals with body temperatures of 42° C. or above combined with any of the following symptoms: loss of appetite, heavy breathing, depression, hanging head, stiff gait, exaggerated blinking, chewing movements, anorexia and signs of nervous symptoms were treated with Terramycin®100 (1 ml/10 kg). These animals were regarded as non-survivors.

IFN-γ ELISpot Assay

Sheep were bled before immunisation, before challenge as well as 13 or 15 and 16 or 20 days after challenge. PBMC were isolated from whole blood as described by Liebenberg et al., 2012 at the set points. PBMC were stimulated with a cocktail of appropriate E. ruminantium peptides (10 µg/ml). ELISpot assay was performed in triplicate wells using the Bovine IFN-γ ELISpotPLUS kit (Mabtech) following the instructions of the manufacture. Briefly, stimulated PBMC ($2 \times 10^5$ PBMC/well) were seeded in pre-coated plates and incubated for 48 h at 37° C. in a humidified 5% CO2 incubator. Plates were developed and spot forming cells (SFC) were enumerated using the Zeiss® KS ELISPOT Reader.

Analysis of CD4+ and CD8+ T Cell Expressing CD45RO+

PBMC were stimulated with a cocktail of appropriate E. ruminantium peptides (10 µg/ml) for 48 h at 37° C. The cells were transferred to a 96-well v-bottomed plate and pelleted. The cells were stained and incubated with the following commercial monoclonal antibodies: CD4 (IgM), GC50A; CD8 (IgG1), CACT80C; CD45RO (IgG3), GC44A, (VMRD) at a 1:100 dilution in PN buffer (PBS, 0.5% FBS containing 0.2% sodium azide). Following washing; secondary antibodies goat anti-mouse IgM-APC (Biorad), goat anti-mouse IgG1-PE (Serotec) and goat anti-mouse IgG3-FITC (Biorad) were added at a dilution of 1:10, 1:40 and 1:10 respectively. All incubations were for 15 min at room temperature and washing was done twice with PN buffer. Cells were fixed with 0.2% formaldehyde in PBS. Samples were assayed on a FC 500 Beckman Coulter® cytometer. Analysis of data was done using the Kuluza software version 1.2 (Beckman Coulter®).

TABLE 4

Summary of sheep treatment

| Experiment | Treatment | Number of sheep/group | Dose and route of administration |
|---|---|---|---|
| Animal trial 1 | Empty vector | 5 | 200 µg IM; 50 µg gg[a] |
| | Empty vector + adjuvant | 5 | 200 µg IM; 50 µg gg with 20 µl adjuvant topically |
| | pLamp + adjuvant (gg) and pLamp IM no adjuvant | 5 | 200 µg IM; 50 µg gg with 20 µl adjuvant topically |
| | pSignal plus + adjuvant (gg) and pSignal IM no adjuvant | 5 | 200 µg IM; 50 µg gg with 20 µl adjuvant topically |
| | Naive | 2 | None |
| | Positve control (infection and treatment) | 2 | |
| Animal trial 2 | Empty vector co-administered with adjuvant | 2 | 200 µg IM co-administered with adjuvant; 50 µg gg with 20 µl adjuvant topically |
| | Adsorbed Empty vector co-administered with adjuvant | 5 | 250 µg SC co-administered with adjuvant |
| | pLamp co-administered with adjuvant | 5 | 200 µg IM co-administered with adjuvant; 50 µg gg with 20 µl adjuvant topically |
| | pME1 co-administered with adjuvant | 5 | 200 µg IM co-administered with adjuvant; 50 µg gg with 20 µl adjuvant topically |
| | pME2 co-administered with adjuvant | 5 | 200 µg IM co-administered with adjuvant; 50 µg gg with 20 µl adjuvant topically |
| | Adsorbed pME2 co-administered with adjuvant | 5 | 250 µg SC co-administered with adjuvant |
| | Naive | 2 | None |

[a]gg = intradermal immunisation using a gene gun

Statistical Analysis

The significance of differences between the RI scores and ELISpot assay results were determined by means of the Student's t-test. Differences were considered significant at a p value of <0.01.

Figure 5:
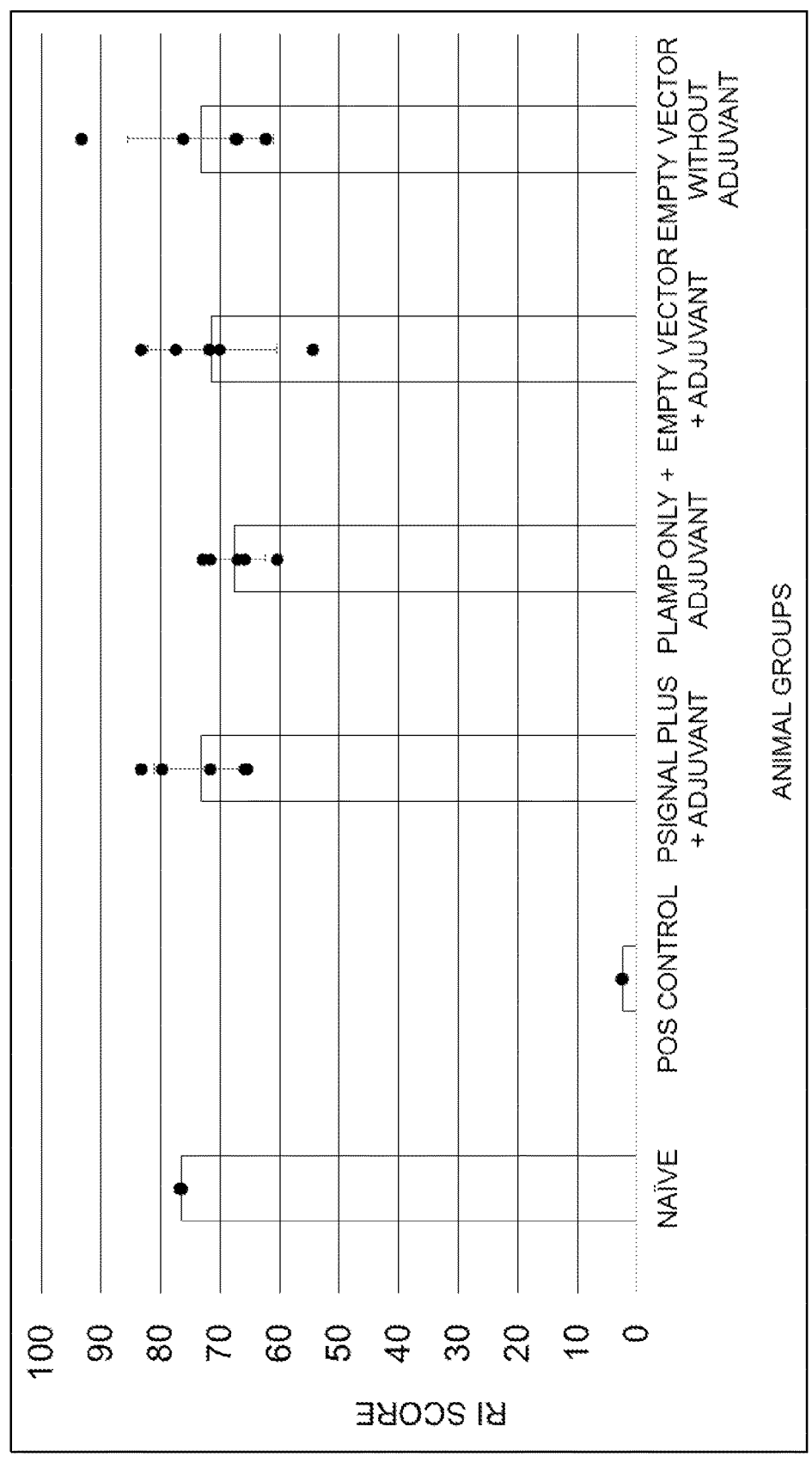
FIG. 5: Average RI score of sheep immunised with pSignal plus or pLamp plus MPLA adjuvant, compared to sheep immunised with the empty vector plus adjuvant. Sheep were immunised using both the IM injection and intradermal inoculation with the gene gun while the adjuvant was applied topically on the gene gun inoculation site. Sheep were challenged with heartwater-infected ticks. The dots represent the RI score of each sheep in the group.

Evaluation of the Protective Efficiency of Multi-Epitope DNA Vaccines Following Tick Challenge During immunisation, the sheep in trial 1 received their adjuvant topically at the gene gun inoculation sites. Five weeks after the third DNA inoculation, sheep were infected with heartwater by allowing infected ticks to feed on them. None of the sheep immunised with the pLamp and pSignal plus multi-epitope vaccines survived challenge (Table 2). These animals showed critical temperature increases between 14 and 20 days post infection (dpi). This was accompanied by severe heartwater symptoms as shown by higher RI values (FIG. 5). Sheep inoculated with pLamp, had RI values of between 66 and 72 (Ave 68±5.0) while those immunised with pDNA Signal plus had RI values of between 66 and 83 (Ave 73±8.0). Additionally, there was no significant RI differences between animals in these groups and their respective negative controls. All the sheep in the negative control and naïve groups succumbed to infection. The animals inoculated with the empty vector only; started showing temperature increases 14 and 16 dpi. While the sheep that received the empty vector with the adjuvant started showing critical temperature increases between 16 and 23 dpi.

Evaluation of Ag-Specific Immune Responses to Vaccination with Multi-Epitope DNA Vaccine Constructs Following Tick Challenge Cellular immune responses play a critical role in protective immunity against heartwater infection. To evaluate if the above multi epitope DNA vaccines can induce specific T cell responses, IFN-γ ELISPOT assay was performed using PBMC isolated before challenge (five weeks after the third inoculation) as well as 13 and 16 days after challenge (Table 5). When sheep were immunised with pLamp, only sheep 3297 showed significant IFN-γ production after immunisation prior to tick challenge. After the sheep were tick challenged, sheep 3335 and 3328 showed significant IFN-γ responses 13 and 16 days post infection respectively. Although sheep 3297 and 3315 showed an increase in the number of IFN-γ producing cells; these were not significantly different from responses induced in unstimulated PBMC. When sheep were immunised with pSignal plus, only sheep 3303 showed significant Ag-specific IFN-γ production before challenge. After challenge, there was no significant IFN-γ production observed in the sheep in this group.

In addition to IFN-γ responses, the number of CD4+ and CD8+ T cells expressing memory markers (CD45RO+) were measured by flow cytometry post vaccination as well as post tick challenge (Table 5). Five weeks after immunisation with pLamp, only one sheep (3338) showed 19% increase in the number of CD4+ T cells expressing CD45RO+. After the sheep were exposed to tick challenge, sheep 3315 and 3328 showed five and two percent increase respectively in the number of these cells 13 dpi. The remaining sheep showed no increase and this was also observed with the sheep that were inoculated with the empty vector. Sixteen days after tick challenge, only sheep 3315 showed a 5% increase in the percentages of CD4+ T cells expressing CD45RO+. Sheep that were immunised with the pSignal plus construct showed no induction of CD4+ T cells expressing CD45RO+ before and after challenge. Only sheep 3314 had a 13% increase of these cells 16 days after tick challenge. The number of CD8+ T cells expressing CD45RO+ was also measured as above. Sheep inoculated with pLamp showed similar percentages of CD8+ T cells expressing CD45RO+ to those of sheep immunised with the empty vector. Thirteen days after tick challenge, sheep 3315 showed the highest percentage of these cells while the other sheep showed percentages that were similar to those of the sheep in the negative control group. Animals immunised with pSignal plus construct had lower percentages of CD8+ T cells expressing CD45RO+ compared to sheep inoculated with the empty vector both before and 13 days after challenge. Sixteen days post tick challenge, these sheep showed higher percentages of these cells.

Animal Trial 2

In animal trial 2, in addition to topical application at the gene gun inoculation site, the adjuvant was also co-administered with the DNA vaccine via IM route. Six groups of sheep (Table 4) were immunised three times in three weeks' interval with: 1. Empty vector (pCDNA3.1(+) vector) co-administered with adjuvant, 2. Adsorbed empty vector co-administered with adjuvant, 3. pLamp co-administered with adjuvant, 4. pME1 co-administered with adjuvant, 5. pME2 co-administered with adjuvant, 6. Adsorbed pME2 co-administered with adjuvant. The sheep that were inoculated with the naked pDNA received 200 µg pDNA co-administered with adjuvant by IM injection and 50 µg pDNA intradermally by the gene gun as above. While the sheep inoculated with adsorbed pDNA received 250 µg pDNA co-administered with adjuvant by subcutaneous injection. Additional control groups were the non-immunised naïve sheep (n=2) and the positive control (n=2) that were infected and treated as above. Five weeks after the third DNA inoculation, all the sheep were tick challenged with *E. ruminantium* infected adult ticks and monitored as described above.

Figure 6:
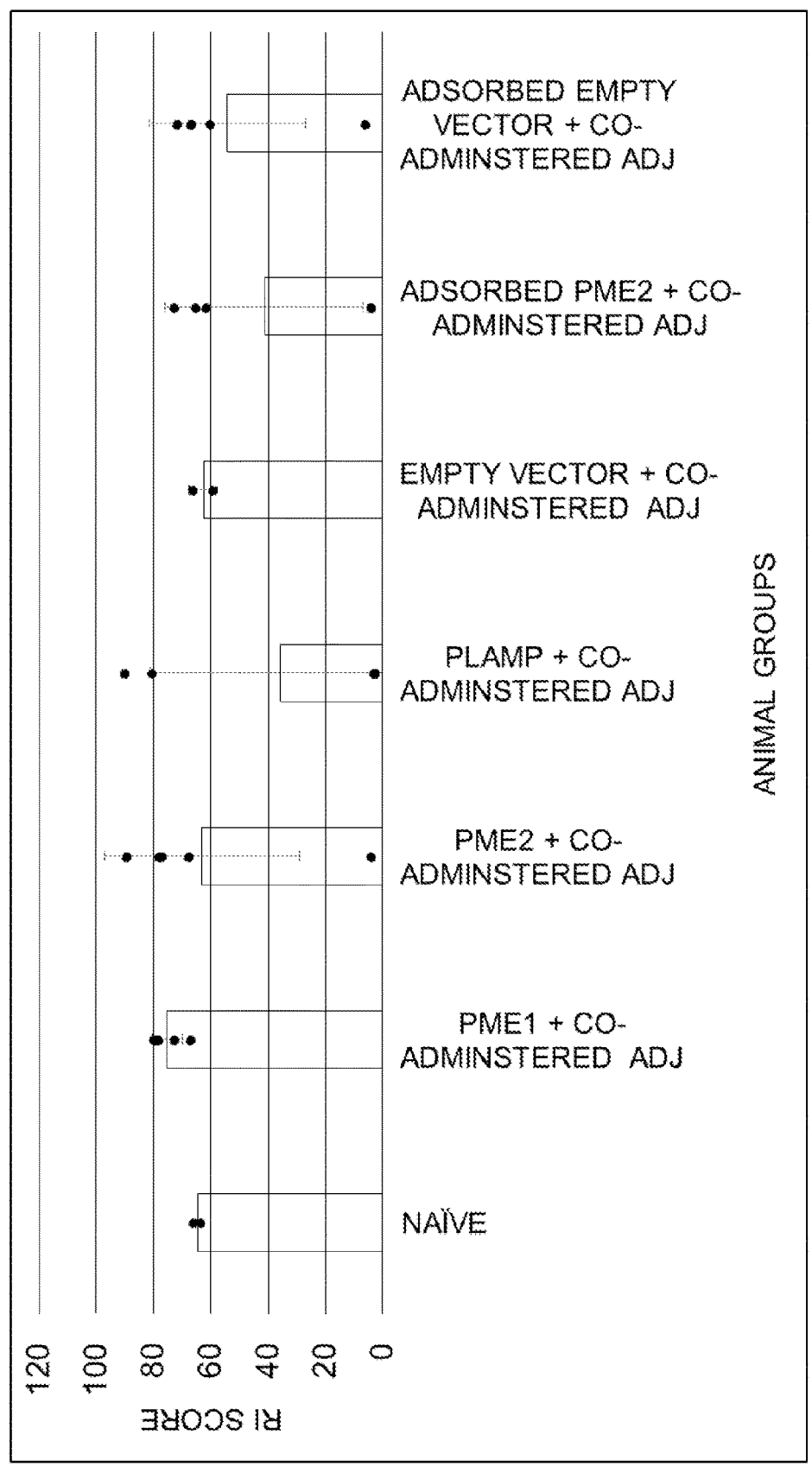
FIG. 6: Average RI score of sheep immunised with pLamp, pME1 and pME2, pME2 adsorbed to microparticles co-administered with MPLA adjuvant, compared to sheep immunised with naked or adsorbed empty vector co-administered with adjuvant. Sheep were immunised using both the IM injection and intradermal inoculation with the gene gun while the adjuvant was co-administered with the vaccine via IM inoculation. Sheep were challenged with heartwater-infected ticks. The dots represent the RI score of each sheep in the group.

Evaluation of the Protective Efficiency of a Multi-Epitope DNA Vaccine Co-Administered with an Adjuvant and/or Adsorbed to Biodegradable MP Following Tick Challenge In the second animal trial an additional two DNA vaccine constructs were tested together with the pLamp construct and these were the pME1 and pME2 constructs. Unlike in animal trial 1; all the DNA vaccines were co-administered with the MPL adjuvant when delivered via the gene gun and IM route. When sheep were immunised with pLamp co-administered with adjuvant, three of the five sheep survived tick challenge (Table 3). The two sheep (3299 & 3333) that succumbed to infection, had increased body temperature as well as severe heartwater symptoms as shown by RI of 80 and 90 respectively. While the three sheep that survived, sheep 3488, 3498 and 3337 showed no temperature increases or heartwater symptoms as shown by RI of 3 for each animal (Table 3, FIG. 5). None of the sheep that were immunised with pME1 co-administered with adjuvant survived challenge (Table 3). The animals in this group started showing critical temperature increases between 16 and 29 dpi and this was accompanied by severe heartwater symptoms with RI values of between 67 and 80 (75±5.0) (FIG. 6, Table 3). While immunising with pLamp-2 co-administered with adjuvant resulted in one of the five sheep surviving tick challenge. The four sheep (3309, 3482, 3495, and 3324) that did not survive challenge had increased body temperatures between 16 and 18 dpi with RI scores of between 67 and 89. While the surviving sheep 3332, showed no temperature increase or heartwater symptoms with RI score of 4 (FIG. 6, Table 3). All the sheep in the negative control and naïve groups succumbed to the disease. When pME2 construct was adsorbed onto PLGA microparticles and co-administered SC with the adjuvant, two of the five sheep survived tick challenge. The three sheep that did not survive; sheep 3501, 3485 and 3487 started having critical rise in temperature on day 17, 25 and 28 after challenge respectively. These animals showed mild to severe heartwater symptoms with RI scores of between 61 and 73. The two animals that survived tick challenge, sheep 3491 and 3316, showed no temperature increases or heartwater symptoms as shown by RI scores of 4 for each sheep. The corresponding negative control group that was immunised with the empty vector adsorbed onto PLGA microparticles and co-administered SC with the adjuvant had one of the five sheep survive challenge. This animal (sheep 3484) had no temperature reaction nor heartwater symptoms (RI score=6) while the four animals that succumbed to the disease did. These sheep started showing temperature increases between 16 and 28 days after tick challenge with RI scores of between 60 and 72 (FIG. 6, Table 3).

Evaluation of Ag-Specific Immune Responses to Vaccination with Multi-Epitope DNA Vaccine Constructs Co-Administered with an Adjuvant and/or Adsorbed to Biodegradable MP Following Tick Challenge Ag-specific IFN-γ responses and the number of CD4+ and CD8+ T cells expressing memory markers (CD45RO+) were measured after vaccination (before challenge) as well as 15 and 20 days after tick challenge (Table 6). When sheep were immunised with pLamp co-administered with adjuvant, one sheep (3337) showed a significant number of

TABLE 5

Ag-specific IFN-γ responses and percentages of memory CD4+ and CD8+ T cells from sheep immunised with different DNA vaccine constructs. Responses were determined before challenge, 13 and 16 days after tick challenge.

| Treatment | Sheep number | Number of Spmc$^a$ | | | % of CD4+CD45RO+ | | | % of CD8+CD45RO+ | | |
| --- | --- | --- | --- | --- | --- | --- | --- | --- | --- | --- |
| | | Before challenge | 13 days after challenge | 16 days after challenge | Before challenge | 13 days after challenge | 16 days after challenge | Before challenge | 13 days after challenge | 16 days after challenge |
| Empty vector + adjuvant | 3295 | 58 ± 1.4* | 10 ± 3.5 | 88 ± 8.5 | 0 | 0 | 2 | 0 | 14 | 13 |
| | 3321 | 28 ± 2.8 | 5 ± 0.7 | 58 ± 2.1 | 0 | 0 | 0 | 14 | 0 | 9 |
| | 3304 | 25 ± 1.4 | 23 ± 1.4 | 5 ± 2.8 | 0 | 0 | 15 | 7 | 0 | 30 |
| | 3329 | 0 | 0 | 108 ± 9.9 | 0 | 0 | 5 | 0 | 7 | 23 |
| | 3300 | 15 ± 3.5 | 13 ± 5.7 | 53 ± 2.8 | 0 | 0 | 0 | 26 | 0 | 3 |
| pLamp + adjuvant | 3297 | 52.5 ± 2.1* | | 255 ± 19.8 | 0 | 0 | 0 | 0 | 5 | 0 |
| | 3315 | 25 ± 4.2 | 37.5 ± 0.0 | 625 ± 14.1 | 0 | 5 | 5 | 6 | 37 | 27 |
| | 3335 | 0 | 9.25 ± 0.7* | 8 ± 3.5 | 0 | 0 | 0 | 23 | 16 | 16 |
| | 3328 | 22.5 ± 2.8 | 45 ± 8.5 | 133 ± 1.4* | 0 | 2 | 0 | 0 | 0 | 0 |
| | 3338 | 0 | 7.5 ± 3.5 | 0 | 19 | 0 | 0 | 19 | 0 | 0 |
| pSignal plus + adjuvant | 3303 | 45 ± 2.1* | 3 ± 3.5 | 25 ± 5.7 | 0 | 0 | 0 | 0 | 0 | 0 |
| | 3318 | 60 ± 1.4 | 28 ± 2.1 | 113 ± 12.7 | 0 | 0 | 0 | 0 | 0 | 18 |
| | 3323 | 10 ± 4.2 | 8 ± 0.7 | 13 ± 2.8 | 0 | 0 | 0 | 9 | 0 | 31 |
| | 3327 | 20 ± 4.9 | 0 | 48 ± 7.1 | 0 | 0 | 0 | 0 | 1 | 43 |
| | 3314 | 0 | 0 | 93 ± 6.4 | 0 | 0 | 13 | 0 | 0 | 55 |

$^a$The number of IFN-γ producing cells was expressed as spots per million cells (Spmc). Ag-specific Spmc of the immunised sheep were compared to the Spmc obtained from unstimulated PBMC. Only Ag-specific Spmc that were twice or more than the Spmc of the unstimulated PBMC and had significant p values (*p ≤ 0.01 as determined by Student t-test) were regarded as a positive response.

IFN-γ producing cells before and 15 days after challenge. Although sheep 3498 had very high number of IFN-γ producing cells, these were not significantly different from the responses observed in the unstimulated PBMC. Additionally, this sheep as well as sheep 3488 showed an increase in their IFN-γ responses 15 days after challenge and these were the sheep that survived tick challenge. While the sheep that succumbed to the disease showed a decrease in these responses after tick challenge (Table 6). In the group that was inoculated with pME1 co-administered with adjuvant, four sheep showed significant IFN-γ responses before challenge and two of these had positive responses after challenge. However, all the sheep in this group succumbed to infection. When sheep were inoculated with pME2 co-administered with adjuvant, two sheep showed significant Ag-specific IFN-γ responses 15 days after challenge. In addition to these two sheep, there was an increase of these responses after challenge in two more sheep and one of them was sheep 3332 which survived tick challenge. In the group that was inoculated with pME2 construct adsorbed onto PLGA microparticles and co-administered SC with the adjuvant (Table 6), two sheep showed significant number of IFN-γ producing cells before challenge. However, these sheep showed a decrease in these cells after tick challenge and these were part of the non-survivors. Although sheep 3316, showed a high number of IFN-γ producing cells before challenge, these was not significantly different from the responses induced in unstimulated PBMC. After tick challenge, this sheep showed significant IFN-γ responses and it was one of the two survivors.

Another sheep that survived (3491), had responses that were not significantly different from the responses induced in unstimulated PBMC but showed an increase in these responses after tick challenge.

The number of CD4+ and CD8+ T cells expressing memory markers (CD45RO+) were measured also in these animals using flow cytometry. In the group of sheep inoculated with pLamp co-administered with adjuvant, three sheep (3299, 3488 and 3498) had between 2.7 and 5.9% increase in the number of memory CD4+ T cells before challenge. After challenge, sheep 3299, 3333 and 3337 had between 11.0 and 37.6% increase in the number of these cells. Only sheep 3337, showed an increase again 20 days post challenge. Of these animals; sheep 3488, 3498 and 3337 survived tick challenge. When measuring CD8+ T cells expressing CD45RO+, all the sheep showed an increase in the number of these cells before challenge with percentage increases of between 1.8 and 63.0. The same was observed 15 days after challenge with percentage increases of between 8.9 and 54.5. Twenty days after challenge, only sheep 3488 and 3337 showed percentage increases in the number of these cells. Two of the sheep (3322 and 3325) that were inoculated with pME1 co-administered with adjuvant showed a slight increase in the number of CD4+ T cells expressing CD45RO+ before challenge. While after challenge three sheep (3302, 3322 and 3494) showed an increase of between 3.4 and 34.9%. Again when the number of CD8+ T cells expressing CD45RO+ were measured before and after challenge (16 days) three sheep (3322, 3494 and 3293)

TABLE 6

Ag-specific IFN-γ responses and percentages of memory CD4+ and CD8+ T cells from sheep immunised with different DNA vaccine constructs co-administered with adjuvant. Responses were determined before challenge, 15 and 20 days after tick challenge.

| | | Number of Spmc[a] | | | % of CD4+CD45RO+ T cells | | | % of CD8+CD45RO+ T cells | | |
|---|---|---|---|---|---|---|---|---|---|---|
| Treatment | Sheep number | Before challenge | 15 days after challenge | 20 days after challenge | Before challenge | 15 days after challenge | 20 days after challenge | Before challenge | 15 days after challenge | 20 days after challenge |
| Empty vector co-administered with adjuvant | 3499 | 10 ± 1.4 | 68 ± 6.4 | nd | | | | | | |
| | 3320 | 60 ± 17 | 68 ± 9.9 | 98 ± 5.7 | | | | | | |
| Adsorbed Empty vector co-administered with adjuvant | 3489 | 0 | 8 ± 2.8 | 0 | 0 | 0 | 73.13 | 18.21 | 0 | 211.07 |
| | 3493 | 78 ± 8.5 | 18 ± 2.1 | | 0 | 0 | Nd | 26.33 | 9.01 | nd |
| | 3483 | | | 0 | 3.63 | 36.63 | 0 | 20.07 | 43.37 | 0 |
| | 3484 | 145 ± 0.0* | 8 ± 8.5 | 0 | 3.57 | 13.36 | 0 | 0 | 0 | 0 |
| | 3490 | 0 | 0 | 0 | 5.34 | 16.57 | 0 | 48.02 | 28.82 | 62.69 |
| pLamp co-administered with adjuvant | 3299 | 50 ± 6.4 | 5 ± 4.2 | nd | 2.77 | 37.63 | Nd | 4.84 | 50.00 | nd |
| | 3488 | 25 ± 3.5 | 38 ± 3.5 | 30 ± 3.5 | 5.94 | 0 | 1.15 | 36.38 | 9.71 | 3.13 |
| | 3333 | 33 ± 5.7 | 0 | nd | 0 | 17.42 | Nd | 30.24 | 54.45 | nd |
| | 3498 | 15 ± 2.1 | 145 ± 9.9 | 40 ± 2.8 | 3.96 | 0 | 0 | 63.00 | 29.58 | 0 |
| | 3337 | 20 ± 0.4* | 60 ± 1.4* | 15 ± 2.6 | 0 | 11.02 | 16.38 | 38.70 | 6.97 | 52.04 |
| pME1 co-administered with adjuvant | 3302 | 183 ± 15.6 | 143 ± 12.7 | nd | 0 | 34.95 | Nd | 0 | 32.23 | nd |
| | 3322 | 248 ± 1.4* | 50 ± 0.0* | 0 | 1.16 | 20.65 | Nd | 38.35 | 0 | nd |
| | 3325 | 173 ± 4.2* | 238 ± 2.8* | 120 ± 3.5* | 4.47 | 0 | 0 | 0 | 0 | 5.71 |
| | 3494 | 120 ± 4.9* | 125 ± 7.1 | 0 | 0 | 3.95 | 43.80 | 7.46 | 43.30 | 166.88 |
| | 3293 | 118 ± 3.5* | 43 ± 0.7 | nd | 0 | 0 | Nd | 4.54 | 5.29 | nd |
| pME2 co-administered with adjuvant | 3389 | 53 ± 5.7 | 20 ± 2.8 | nd | 0 | 57.95 | Nd | 17.58 | 54.29 | nd |
| | 3482 | 0 | 105 ± 7.8 | 0 | 10.73 | 26.38 | 0 | 48.90 | 37.68 | 80.19 |
| | 3332 | 0 | 10 ± 0.7 | 13 ± 0.0 | 0 | 85.40 | 2.00 | 0 | 86.24 | 237.25 |
| | 3495 | 3 ± 1.4 | 33 ± 0.7* | nd | 275.45 | 105.96 | Nd | 190.34 | 42.69 | nd |
| | 3324 | 5 ± 0.7 | 48 ± 0.7* | 0 | 2.51 | 3.79 | 0 | 24.27 | 29.06 | 36.90 |
| Adsorbed pME2 co-administered with adjuvant | 3487 | 85 ± 0.7* | 33 ± 1.7 | 0 | 7.63 | 8.59 | 38.87 | 13.73 | 62.22 | 18.75 |
| | 3491 | 8 ± 3.5 | 43 ± 2.8 | 3 ± 2.8 | 0 | 68.83 | 17.65 | 7.64 | 65.46 | 6.15 |
| | 3316 | 1110 ± 70.7 | 80 ± 3.5* | 20 ± 3.5 | 3.37 | 54.37 | 13.52 | 27.62 | 17.26 | 64.47 |
| | 3581 | 60 ± 2.8* | 28 ± 3.5 | 10 ± 1.4 | 6.60 | 21.38 | 0 | 49.32 | 82.17 | 5.25 |
| | 3485 | 43 ± 4.9 | 153 ± 4.9 | 113 ± 35.4 | 0.71 | 79.50 | 165.42 | 23.21 | 123.29 | 82.28 |

[a]The number of IFN-γ producing cells was expressed as spots per million cells (Spmc). Ag-specific Spmc of the immunised sheep were compared to the Spmc obtained from unstimulated PBMC. Only Ag-specific Spmc that were twice or more than the Spmc of the unstimulated PBMC and had significant p values (*p ≤ 0.01 as determined by Student t-test) were regarded as a positive response.

in this group showed increases in the number of these cells. Twenty days after challenge two sheep (3325 and 3494) showed increases in the number of memory CD8+ T cells even though all the animals in this group succumbed to infection. When sheep were inoculated with pME2 co-administered with adjuvant, three sheep showed an increase in the number of CD4+ T cells expressing CD45RO before challenge. Fifteen days after challenge, all the sheep in this group showed increases of between 3.8 and 106.0%. While 20 days post challenge only 1 surviving sheep (3332) showed a slight increase although this was lower that the increase observed 15 days post challenge. When the number of memory CD8+ T cells was measured, four sheep (with the exception of the sheep 3332) had between 17.6 and 190.3% increase in the number of these cells before challenge. After challenge all the sheep showed an increase in the number of these cells. Three of the five sheep (3487, 3316 and 3501) that were inoculated with pME2 construct adsorbed onto PLGA microparticles co-administered with adjuvant, showed a slight increase in number of memory CD4+ T cells before challenge. Fifteen days after tick challenge, all the sheep showed an increase of between 8.6 and 79.5%. Although 20 days post challenge this increase was maintained in three sheep; the two sheep that survived challenge (3491 and 3316) showed a drop in the number of this cells compared to 15 days post challenge. When memory CD8+ T cells were analysed, all the sheep in this group showed an increase in the number of these cells before and after challenge.

This is the first DNA vaccine trial where E. ruminantium infected ticks were used to challenge the animals in the laboratory. Here, two vaccine constructs were tested, namely pSignal Plus and pLamp. However, none of these constructs could protect sheep against tick challenge. MPL has the ability to induce innate immune responses as well as migration and maturation of dendritic cells (DC) in situ. However, MPL is one of the adjuvants that are undesirable for transcutaneous immunisation or topical application due to its inability to cross the stratum corneum, the uppermost layer of the skin which is often impermeable to water-soluble macromolecules. Often molecules that can be transported across the stratum corneum can be taken up by Langerhans cells which will then migrate to the draining lymph node followed by differentiation into mature DC which will stimulate neighbouring T lymphocytes. It is this DC located in the subepidermal layer of the skin and other non-immune cells like keratinocytes that seems to play an important role in activation of immune responses after gene gun immunisation. In our case, delivering MPL via topical application might have affected its ability to access these important cells. Thus topical application alone might have not been the best way of administering this adjuvant. It has been shown that co-application of this adjuvant with the vaccine antigen is vital for induction of a successful immune response during transcutaneous immunisation.

In the second animal trial, pLamp in addition to two new DNA vaccine constructs (namely, pME1 and pME2) were tested. In addition to topical application at the gene gun inoculation site, MPL was also co-administered with the DNA vaccine when delivered via IM route. The pLamp construct which was not effective when MLP was applied topically, showed protection of three out of five sheep when co-administered with MPL. The pME2 construct protected one of the five sheep while pME1 did not protect any of the sheep upon tick challenge. Changing the presentation and administration route of the adjuvant significantly enhanced the protective efficiency of pLamp construct. A study by Didierlaurent et al., 2009 investigated the adjuvant activity of AS04 which is made of MPL adsorbed to aluminium salt. The authors showed that the adjuvant and the vaccine antigen should be injected at the same IM site in order to elicit effective adjuvant activity and this had to be done in less than 24 hours. Additionally, MPL was primarily responsible for the innate immune responses induced which were limited to the site of injection and regional lymph nodes (Didierlaurent et al., 2009). The improvement of the protective efficiency of pLamp by co-administration with MPL indicates the importance of inducing innate immunity for successful vaccination against heartwater.

Although pME2 construct was made up of the same epitopes as pLamp in addition to the five new epitopes, it was not as effective as pLamp. This construct was made up of a combination of epitopes from pLamp and pME1. pLamp contained CTL epitopes, namely, Erum2540-21, 2540-6, 2540-16, 2540-19 and 2540-p20 and seven CD4 epitopes, namely Erum7140-6, 7140-7, 7140-20, 7350-9, 7620-12, 8010-8 and 7320-21. While pLamp-1 contained one CTL epitope (Erum0660-42) and five CD4 epitopes (Erum5421-13, 5420-14, 1150-18, 1150-19 and 7360-8). The role of CD4+T lymphocytes in protective immunity against E. ruminantium is well documented and this is the case with the IFN-γ producing activity of CD8+ T cells in protective immunity. It has also been shown that both CD8+ and CD4+ T cells produces IFN-γ and CD8+ T cells requires the help of CD4+ T cells to produce IFN-γ. Interestingly, in addition to inducing cytotoxic activity in vitro, the five CTL epitopes induced IFN-γ production in CD8+ T cells. At the moment the role of the cytotoxic activity of CD8+ T cells in protective immunity against E. ruminantium is unknown. In other related organisms of the species Rickettsia, protection is conferred in part by the cytotoxic activity of CD8+ T cells and to a lesser extent by their IFN-γ producing activity. In a murine model of E. muris, CD8 T lymphocytes were shown to exhibit cytotoxic activity against Ehrlichia-infected target cells; while there was also evidence of IFN-γ production by these cells and CD4+ T cells. In case of E. ruminantium, adoptive transfer of protective immunity was depended on CD8+ and not CD4+ T cells, while in another study there was evidence that CD8+ T cell knockout mice are less susceptible to E. ruminantium infection than CD4+ T cell knockout and normal mice supporting the important role of CD4+ cells.

The Applicant has found that having both the CD8+ and CD4+ epitopes in one construct had a positive effect on the protective efficiency of the vaccine. However; whether protection mediated by CD8+ T cell during E. ruminantium infection is by their cytotoxic or IFN-γ activities or both is unclear and requires further investigation. The other major difference between pLamp, pME1 and pME2 was the plasmid backbone. pLamp contained a LAMP sequence for MHC II targeting that the other two did not have. Instead pME1 and pME2 contained the pentapeptide KFERQ. This KFERQ motif found in substrate proteins, is recognised by Hsc70 for recruitment of the proteins to the lysosomal outer membrane. There LAMP which is a receptor for substrate proteins is responsible for the translocation of these proteins across the lysosomal membrane into the lumen of the lysosome where degradation will occur. The presence of the LAMP sequence in the pLamp construct had a positive effect on the effectivity of this construct. Several anti-HIV vaccine studies have shown that the presence of LAMP in the DNA vaccine constructs often results in enhanced memory CD4+ and CD8+ T cell responses. This seemed to be dependent on targeting the antigen to the endosomal pathway.

In addition to the inclusion of MPL adjuvant in the vaccine formulation, pME2 was also adsorbed onto PLGA biodegradable microparticles. In this form, pME2 protected two of the five tick challenged sheep. However, one of the animals inoculated with the adsorbed empty vector also survived challenge. Biodegradable microparticles are known to have immunostimulatory properties like the activation of dendritic cell maturation and induction of pro-inflammatory cytokines when used alone or in combination with subunit vaccines. Together with the innate immune activation by MPL adjuvant, these responses could have been enough to protect the sheep against challenge. The sheep that succumbed to infection which were inoculated with the adsorbed vaccine or adsorbed empty vector survived the longest, taking on average 25 days to show serious cause of disease. In our case it is not known whether innate immune responses were induced and in future such responses should be evaluated. Another possible explanation for the survival of this sheep could be the animal was not successfully challenged but this can be ruled out since the infectivity of the ticks was determined prior to challenge. It could be possible that the challenge dose was not high enough to induce a serious case of disease since this sheep did not show any of the heartwater symptoms. Additionally, Ag-specific proliferation of memory CD4+ T cells was induced in this sheep after challenge showing that the sheep was exposed to the pathogen and its immune system reacted to the antigen. The use of biodegradable microparticles as carriers often results in improved efficiencies of DNA vaccines. This has been reported for disease of veterinary importance like Swine influenza, foot and mouth disease, infectious bursal disease. In our case, adsorbing pME2 onto PLGA microparticles partially improved the efficacy of this construct. Additionally, these animals had on average, the highest percentages of memory CD4+ and CD8+ T cells. Since formulating pME2 with biodegradable microparticles improved its efficiency, maybe formulating our most effective construct (pLamp) with biodegradable microparticles would have given complete protection and this will be investigated in future. It is documented that physiochemical properties of biodegradable particles influence their overall performance. Properties like size, charge and fabrication methods used can influence even the type and magnitude of immune responses that the particles induce. The microparticles formulated in this study were between 5.0 μm-20 μm in size. Some studies have shown that microparticles are often not easily taken up by DC as efficiently as nanoparticles. Instead microparticles often attach to the cell surface and release the antigen which is then taken up by the cells. As such, nano-sized particles which can be readily taken up by antigen presenting cells can activate these cells efficiently. Biodegradable nanoparticles can serve as successful vaccine vectors however further studies into their physiochemical properties are required in order to use them efficiently in our future DNA vaccine formulation.

Cellular immune responses induced in the vaccinated sheep were also evaluated throughout the trial. There was evidence of IFN-γ production in PBMC from immunised sheep even in the groups where the animals did not survive tick challenge. A challenge study in goats showed that IFN-γ could be used as an indicator for protective immunity. However, this was not the case in our study; some of the sheep that survived challenge (3488, 3498, 3332, and 3491) showed no significant IFN-γ production while some did (3337 and 3316). Previous heartwater challenge studies have also observed that there is often lack of correlation between IFN-γ production and protective immunity. It is therefore our opinion that IFN-γ alone cannot be used as an indicator for protective immunity against E. ruminantium, thus there is a need to identify additional correlates of protective immunity.

In addition to IFN-γ, we analysed memory T lymphocytes in the vaccinated sheep. Although all the sheep from animal trial 1 succumbed to tick challenge, there was evidence of induction of proliferation of memory CD4+ and CD8+ T cells in sheep inoculated with the pLamp construct while those inoculated with pSignal plus showed no detectable amount of CD4+ T cells except for one sheep. Overall the percentages of memory CD8+ T cell were much higher than the percentages of memory CD4+ T cells. In some sheep that survived from trial 2 (3488, 3332, 3491 and 3316), there was an induction of proliferation of these cells both before and after challenge. While some survivors e.g. 3498 and 3337 showed no proliferation before or after challenge respectively. Like the IFN-γ responses, the memory cell responses were also highly variable and also somewhat showing evidence of lack of correlation with protection. The reduction of IFN-γ production by pathogen-specific T lymphocytes could be due to the absence of these cells in circulation during the sampling period. Instead these cells could be in other immunological compartments like lymph nodes and the spleen where E. ruminantium is first detected after challenge before entering the blood stream. Memory T cells specific to E. ruminantium can also leave circulation and enter other immune compartment like the lymph nodes.

Additionally, in our animal trials we use outbred natural hosts which often possess MHC class II genes that are highly polymorphic. Different alleles were observed amongst the different sheep with some being shared amongst the animals. It has been shown that the polymorphism amongst the different alleles can affect their peptide binding abilities. Some alleles that we found were known while others did not correspond with any of the published alleles. Of the six sheep that survived challenge in our trial, only sheep 3488 and 3491 shared a common allele *0203. The allele set *0702; *0703 and allele *0801 as well as two unknown alleles were obtained in the other four survivors. Ag-specific immune responses induced in sheep 3488 and 3491 were somewhat similar. The ovine MHC class II DRB1 (Ovar-DRB-1) alleles have been shown to affect the immune responses to infection where the differences in immune responses were caused by the differences in the alleles. Interestingly none of the surviving sheep shared any alleles with the sheep that were used for the selection of the epitopes. This shows that our epitopes are not MHC restricted and can stand a better chance of protecting a genetically diverse population. In order to improve our understanding of protective immunity to heartwater, transcriptome sequencing will be performed on all the animals that survived tick challenge as well as the naïve sheep. This will aid us in elucidating which immunological pathways contributed to the protection against the disease.

Units which are used in this specification and which are not in accordance with the metric system may be converted to the metric system with the aid of the following conversion factor:

$$1 \text{ psi} = 6,895 \times 10^3 \text{ Pa}$$

REFERENCES

Tshikhudo N, Pretorius A, Putterill J, van Kleef M. Preparation and in vitro characterisation of *Ehrlichia ruminantium* plasmid DNA and proteins encapsulated into and DNA adsorbed onto biodegradable microparticles. Ticks Tick Borne Dis 2010; 1:186-93. doi: 10.1016/j.ttbdis.2010.08.001.

Konnai S, Nagaoka Y, Takesima S, Onuma M, Aida Y. Technical note: DNA typing for ovine MHC DRB1 using polymerase chain reaction-restriction fragment length polymorphism (PCR-RFLP). J Dairy Sci 2003; 86:3362-5.

Steyn H C, Pretorius A, McCrindle C M, Steinmann C M, van Kleef M. A quantitative real-time PCR assay for *Ehrlichia ruminantium* using pCS20. Vet Microbiol 2008; 131:258-65. doi: 10.1016/j.vetmic.2008.04.002.

Pretorius A, Collins N E, Steyn H C, van Strijp F, van Kleef M, Allsopp B A. Protection against heartwater by DNA immunisation with four *Ehrlichia ruminantium* open reading frames. Vaccine 2007; 25:2316-24.

Pretorius A, van Kleef M, Collins N E, Tshikudo N, Louw E, Faber F E, et al. A heterologous prime/boost immunisation strategy protects against virulent *E. ruminantium* Welgevonden needle challenge but not against tick challenge. Vaccine 2008; 26:4363-71. doi: 10.1016/j.vaccine.2008.06.006.

Didierlaurent A M, Morel S, Lockman L, Giannini S L, Bisteau M, Carlsen H, et al. AS04, an aluminum salt- and TLR4 agonist-based adjuvant system, induces a transient localized innate immune response leading to enhanced adaptive immunity. J Immunol 2009; 183:6186-97. doi: 10.4049/jimmunol.0901474. Epub 2009 Oct. 28.

---

What is claimed is:

1. A nucleic acid comprising:
   a sequence encoding *Ehrlichia ruminantium* antigenic epitopes which induce a CD4 immune response having amino acid sequences of SEQ ID NOs:9-16;
   a sequence encoding *Ehrlichia ruminantium* antigenic epitopes which induce a CD8 immune response having amino acid sequences of SEQ ID NOs:17-19 and 72;
   an internal ribosomal sequence; and
   a ubiquitin signal.

2. The nucleic acid of claim 1, further comprising a sequence encoding *Ehrlichia ruminantium* antigenic epitopes which induce a CD4 immune response having amino acid sequences of SEQ ID NOs:20-24 and a sequence encoding *Ehrlichia ruminantium* antigenic epitopes which induce a CD8 immune response having an amino acid sequence of SEQ ID NO:25.

3. The nucleic acid of claim 1, further comprising a sequence encoding a CpG motif.

4. The nucleic acid of claim 1, further comprising a sequence encoding an MEW II targeting peptide.

5. The nucleic acid of claim 1, further comprising a sequence encoding a sheep CXCL1 signal peptide.

6. The nucleic acid of claim 1, further comprising a sequence encoding an IL-3 sheep signal peptide.

7. The nucleic acid of claim 1, further comprising a sequence encoding a KFERQ peptide sequence (SEQ ID NO:40).

8. The nucleic acid of claim 1, further comprising a sequence encoding an Ig Kappa signal peptide.

9. The nucleic acid of claim 1, further comprising a sequence encoding a His tag.

10. The nucleic acid of claim 1, wherein the nucleic acid is operably linked to a promoter sequence, and optionally linked to other regulatory sequences that allow for transcription of a protein encoded by the nucleic acid in a cell.

11. The nucleic acid of claim 10, wherein the cell is an animal cell.

12. A multi-epitope DNA vaccine comprising the nucleic acid of claim 1 and a pharmaceutically acceptable diluent, an excipient or an adjuvant.

13. The multi-epitope DNA vaccine of claim 12, wherein the pharmaceutically acceptable adjuvant is monophosphoryl lipid A.

14. The multi-epitope DNA vaccine of claim 12, wherein a polypeptide expressed from the multi-epitope DNA vaccine is capable of eliciting a protective immune response against heartwater disease.

15. A polypeptide comprising:
   *Ehrlichia ruminantium* antigenic epitopes which induce a CD4 immune response having amino acid sequences of SEQ ID NOs:9-16; and
   *Ehrlichia ruminantium* antigenic epitopes which induce a CD8 immune response having amino acid sequences of SEQ ID NOs:17-19 and 72.

16. The polypeptide of claim 15, wherein the polypeptide has the amino acid sequence of SEQ ID NO:1, SEQ ID NO:2, or SEQ ID NO:4.

17. A method of inducing an immune response against heartwater disease in a subject, comprising administering a therapeutically effective amount of the nucleic acid of claim 1 to the subject.

18. The method of claim 17, wherein the subject is a mammal.

19. The method of claim 17, wherein the subject is selected from the group consisting of cattle, sheep, goats, antelope, and buffalo.

* * * * *

UNITED STATES PATENT AND TRADEMARK OFFICE
CERTIFICATE OF CORRECTION

| | | |
|---|---|---|
| PATENT NO. | : 10,682,403 B2 | Page 1 of 1 |
| APPLICATION NO. | : 16/472153 | |
| DATED | : June 16, 2020 | |
| INVENTOR(S) | : Alri Pretorius | |

It is certified that error appears in the above-identified patent and that said Letters Patent is hereby corrected as shown below:

In the Drawings

In sheet 6 of 6, FIG. 6, Lines 3, 5, 7, 9, 11 and 13 (approx.), delete "ADMINSTERED" and insert -- ADMINISTERED --.

In the Specification

In Column 13, Line 1, delete "Generation@" and insert -- Generation® --.

In Column 14, Line 65 (approx.), delete "(16)" and insert -- (18) --.

In Column 16, Line 65, delete "cytometer" and insert -- flow cytometer --.

In Column 17-18, Line 12, delete "Positve" and insert -- Positive --.

In the Claims

In Column 67, Line 51, Claim 4, delete "MEW II targeting peptide" and insert -- MHC II targeting peptide --.

Signed and Sealed this
Seventeenth Day of November, 2020

Andrei Iancu
*Director of the United States Patent and Trademark Office*

SEQUENCE LISTING

```
<160> NUMBER OF SEQ ID NOS: 73

<210> SEQ ID NO 1
<211> LENGTH: 515
<212> TYPE: PRT
<213> ORGANISM: Artificial sequence
<220> FEATURE:
<223> OTHER INFORMATION: pSignal plus amino acid sequence

<400> SEQUENCE: 1
```

Met Ala Arg Ala Ala Asn Pro Ala Pro Arg Leu Leu Gly Ala Ala Met
1               5                   10                  15

Leu Leu Leu Leu Leu Val Ala Ala Gly Arg Arg Ala Ala Gly Ala Pro
                20                  25                  30

Val Arg Arg Lys Ser Tyr Ala Gly Tyr Gln Thr Leu Glu Leu Asp Lys
            35                  40                  45

Val Glu Leu Pro Lys Thr Arg Ala Arg Glu Thr Ser Ser Asp Ile Thr
        50                  55                  60

Val Ile Ser Asp Gly Pro Gly Pro Gly Lys Ala Glu Asp Lys Val Val
65                  70                  75                  80

Lys Ala Ala Gln Ile Gln Asp Val Pro Gly Pro Gly Pro Gly Val Val
                85                  90                  95

Ser Ile Cys Cys Gln Gly Thr Ser Leu Gly Gly Phe Ser Glu Gly Pro
            100                 105                 110

Gly Pro Gly Thr Lys Leu Lys Arg Met Gly Tyr Lys Ile Tyr Asn Val
        115                 120                 125

Ile Phe Ala Gly Pro Gly Pro Gly Leu Gly Ser Ser Ile Met Ala Ile
    130                 135                 140

Phe Gly Lys Leu Pro Trp Pro Ala Gly Pro Gly Pro Gly Ile Val Ser
145                 150                 155                 160

Ser Asp Thr Ser Asn Asn Gly Ser Val Ala Glu Glu Asn Gly Pro Gly
                165                 170                 175

Pro Gly Val Asn Gln Glu Asn Leu Gly Leu Ile Asn Phe Trp Lys Lys
            180                 185                 190

Lys His His His His His Ser Ser Phe Val Val Leu Ser Gly Tyr
        195                 200                 205

Phe Pro Pro Tyr Cys Arg Leu Leu Ala Met Gly Pro Gly Asn Leu Ala
    210                 215                 220

Leu Ser Ser Arg Ala Phe Leu Gly Val Phe Pro Leu Ser Pro Lys Glu
225                 230                 235                 240

Cys Lys Val Cys Met Ser Arg Lys Gln Phe Leu Trp Lys Leu Leu Glu
                245                 250                 255

Asp Lys Gln Arg Leu Arg Pro Phe Ala Gly Ser Gly Thr Pro His Leu

```
            260                 265                 270
Ala Thr Gly Ala Ser Ala Lys Ser His Val Tyr Lys Ile His Leu
            275                 280                 285

Gln Arg Arg His Asn Pro Ser Ala Thr Leu Val Gly Leu Trp Lys Glu
            290                 295                 300

Ser Asn Gly Ser Pro Gln Ala Tyr Ser Thr Arg Gly Arg Met Pro Arg
305                 310                 315                 320

Arg Tyr Pro Ile Val Trp Asp Leu Ile Trp Gly Leu Gly Ala His Ala
                325                 330                 335

Leu His Val Phe Ser Arg Gly Lys Thr Ser Arg Pro Glu Pro Arg
                340                 345                 350

Gly Arg Gly Phe Pro Leu Lys Val Thr Leu Met Gln Ile Phe Val Lys
                355                 360                 365

Thr Leu Thr Gly Lys Thr Ile Thr Leu Glu Val Glu Pro Ser Asp Thr
            370                 375                 380

Ile Glu Asn Val Lys Ala Lys Ile Gln Asp Lys Glu Gly Ile Pro Pro
385                 390                 395                 400

Asp Gln Gln Arg Leu Ile Phe Ala Gly Lys Gln Leu Glu Asp Gly Arg
                405                 410                 415

Thr Leu Ser Asp Tyr Asn Ile Gln Lys Glu Ser Thr Leu His Leu Val
                420                 425                 430

Leu Arg Leu Arg Gly Ala Asp Leu Lys Asn Arg Thr Ile Asn Ile Gly
            435                 440                 445

Val Glu Phe Arg Ile Gln Asp Gly Ala Ala Tyr His Asp Asn Leu Asn
450                 455                 460

Thr Lys Glu Leu Ser Ile Ser Leu Arg Ile Lys Ala Ala Tyr Ile Pro
465                 470                 475                 480

Gln Glu Lys Val Ile Ile Leu Asn Arg Phe Leu Gln Asp Tyr Val Asn
                485                 490                 495

Gln Glu Asn Leu Gly Leu His His His His His Ser Ser Phe Val
                500                 505                 510

Val Leu Ser
        515

<210> SEQ ID NO 2
<211> LENGTH: 483
<212> TYPE: PRT
<213> ORGANISM: Artificial sequence
<220> FEATURE:
<223> OTHER INFORMATION: pLamp amino acid sequence

<400> SEQUENCE: 2

Met Arg Arg Lys Ser Tyr Ala Gly Tyr Gln Thr Leu Glu Leu Asp Lys
1               5                   10                  15

Val Glu Leu Pro Lys Thr Arg Ala Arg Glu Thr Ser Ser Asp Ile Thr
                20                  25                  30

Val Ile Ser Asp Gly Pro Gly Pro Gly Lys Ala Glu Asp Lys Val Val
            35                  40                  45

Lys Ala Ala Gln Ile Gln Asp Val Pro Gly Pro Gly Pro Gly Val Val
        50                  55                  60

Ser Ile Cys Cys Gln Gly Thr Ser Leu Gly Gly Phe Ser Glu Gly Pro
65                  70                  75                  80

Gly Pro Gly Thr Lys Leu Lys Arg Met Gly Tyr Lys Ile Tyr Asn Val
                85                  90                  95

Ile Phe Ala Gly Pro Gly Pro Gly Leu Gly Ser Ser Ile Met Ala Ile
```

```
            100                 105                 110
Phe Gly Lys Leu Pro Trp Pro Ala Gly Pro Gly Ile Val Ser
            115                 120                 125

Ser Asp Thr Ser Asn Asn Gly Ser Val Ala Glu Glu Asn Gly Pro Gly
            130                 135                 140

Pro Gly Val Asn Gln Glu Asn Leu Gly Leu Ile Asn Phe Trp Lys Lys
145                 150                 155                 160

Lys His His His His His Ser Ser Phe Val Val Leu Ser Gly Tyr
                        165                 170                 175

Phe Pro Pro Tyr Cys Arg Leu Leu Ala Met Gly Pro Gly Asn Leu Ala
                180                 185                 190

Leu Ser Ser Arg Ala Phe Leu Gly Val Phe Pro Leu Ser Pro Lys Glu
                195                 200                 205

Cys Lys Val Cys Met Ser Arg Lys Gln Phe Leu Trp Lys Leu Leu Glu
                210                 215                 220

Asp Lys Gln Arg Leu Arg Pro Phe Ala Gly Ser Gly Thr Pro His Leu
225                 230                 235                 240

Ala Thr Gly Ala Ser Ala Ala Lys Ser His Val Tyr Lys Ile His Leu
                245                 250                 255

Gln Arg Arg His Asn Pro Ser Ala Thr Leu Val Gly Leu Trp Lys Glu
                260                 265                 270

Ser Asn Gly Ser Pro Gln Ala Tyr Ser Thr Arg Gly Arg Met Pro Arg
                275                 280                 285

Arg Tyr Pro Ile Val Trp Asp Leu Ile Trp Gly Leu Gly Ala His Ala
                290                 295                 300

Leu His Val Phe Ser Arg Gly Lys Thr Ser Arg Pro Pro Glu Pro Arg
305                 310                 315                 320

Gly Arg Gly Phe Pro Leu Lys Val Thr Leu Met Gln Ile Phe Val Lys
                325                 330                 335

Thr Leu Thr Gly Lys Thr Ile Thr Leu Glu Val Glu Pro Ser Asp Thr
                340                 345                 350

Ile Glu Asn Val Lys Ala Lys Ile Gln Asp Lys Glu Gly Ile Pro Pro
                355                 360                 365

Asp Gln Gln Arg Leu Ile Phe Ala Gly Lys Gln Leu Glu Asp Gly Arg
370                 375                 380

Thr Leu Ser Asp Tyr Asn Ile Gln Lys Glu Ser Thr Leu His Leu Val
385                 390                 395                 400

Leu Arg Leu Arg Gly Ala Asp Leu Lys Asn Arg Thr Ile Asn Ile Gly
                405                 410                 415

Val Glu Phe Arg Ile Gln Asp Gly Ala Ala Tyr His Asp Asn Leu Asn
                420                 425                 430

Thr Lys Glu Leu Ser Ile Ser Leu Arg Ile Lys Ala Ala Tyr Ile Pro
                435                 440                 445

Gln Glu Lys Val Ile Ile Leu Asn Arg Phe Leu Gln Asp Tyr Val Asn
                450                 455                 460

Gln Glu Asn Leu Gly Leu His His His His His Ser Ser Phe Val
465                 470                 475                 480

Val Leu Ser

<210> SEQ ID NO 3
<211> LENGTH: 424
<212> TYPE: PRT
<213> ORGANISM: Artificial Sequence
<220> FEATURE:
```

-continued

<223> OTHER INFORMATION: pME1 amino acid sequence

<400> SEQUENCE: 3

```
Ser Ser Phe Val Val Leu Ser Met Ser Ser Leu Ser Ile Leu His Leu
1               5                   10                  15

Leu Leu Leu Leu Leu Ser Leu His Arg Arg Lys Ser Tyr Ala Gly Tyr
                20                  25                  30

Gln Thr Leu Lys Phe Glu Arg Gln Gly Pro Gly Pro Gly Asn Gly Ile
            35                  40                  45

Asn Asp Glu Asp Leu Gly Gly Met Tyr Gly Leu Leu Leu Leu Gly Gly
        50                  55                  60

Phe Phe Ser Val Met Gly Pro Gly Pro Gly Val Val Ile Val Met Asp
65                  70                  75                  80

Leu Cys Cys Gln Ile Ala Gly Leu Leu Cys Gly Pro Gly Pro Gly Val
                85                  90                  95

Lys Asn Tyr Leu Asn Gln His Leu Lys Lys Ile Ile Asp Arg Ile Lys
            100                 105                 110

His Ser Asn Leu Asn Ala Ile Gly Pro Gly Pro Gly His His His His
        115                 120                 125

His His Ser Ser Phe Val Val Leu Ser Gly Tyr Phe Pro Pro Tyr Cys
130                 135                 140

Arg Leu Leu Ala Met Gly Pro Gly Asn Leu Ala Leu Ser Ser Arg Ala
145                 150                 155                 160

Phe Leu Gly Val Phe Pro Leu Ser Pro Lys Glu Cys Lys Val Cys Met
                165                 170                 175

Ser Arg Lys Gln Phe Leu Trp Lys Leu Leu Glu Asp Lys Gln Arg Leu
            180                 185                 190

Arg Pro Phe Ala Gly Ser Gly Thr Pro His Leu Ala Thr Gly Ala Ser
        195                 200                 205

Ala Ala Lys Ser His Val Tyr Lys Ile His Leu Gln Arg Arg His Asn
        210                 215                 220

Pro Ser Ala Thr Leu Val Gly Leu Trp Lys Glu Ser Asn Gly Ser Pro
225                 230                 235                 240

Gln Ala Tyr Ser Thr Arg Gly Arg Met Pro Arg Arg Tyr Pro Ile Val
                245                 250                 255

Trp Asp Leu Ile Trp Gly Leu Gly Ala His Ala Leu His Val Phe Ser
            260                 265                 270

Arg Gly Lys Thr Ser Arg Pro Pro Glu Pro Arg Gly Arg Gly Phe Pro
        275                 280                 285

Leu Lys Val Thr Leu Met Gln Ile Phe Val Lys Thr Leu Thr Gly Lys
        290                 295                 300

Thr Ile Thr Leu Glu Val Glu Pro Ser Asp Thr Ile Glu Asn Val Lys
305                 310                 315                 320

Ala Lys Ile Gln Asp Lys Glu Gly Ile Pro Pro Asp Gln Gln Arg Leu
                325                 330                 335

Ile Phe Ala Gly Lys Gln Leu Glu Asp Gly Arg Thr Leu Ser Asp Tyr
            340                 345                 350

Asn Ile Gln Lys Glu Ser Thr Leu His Leu Val Leu Arg Leu Arg Gly
        355                 360                 365

Ala Met Arg Thr Pro Ala Gln Phe Leu Gly Ile Leu Leu Leu Trp Phe
        370                 375                 380

Pro Gly Ile Lys Cys Ala Ala Tyr Asp Ile Arg Ala Ile Leu Ser Val
385                 390                 395                 400
```

Asp Gly Leu Phe Asp Ser Lys Ala Ala Ala Tyr His His His His
                    405                 410                 415

His Ser Ser Phe Val Val Leu Ser
            420

<210> SEQ ID NO 4
<211> LENGTH: 635
<212> TYPE: PRT
<213> ORGANISM: Artificial Sequence
<220> FEATURE:
<223> OTHER INFORMATION: pME2 amino acid sequence

<400> SEQUENCE: 4

Ser Ser Phe Val Val Leu Ser Met Ser Ser Leu Ser Ile Leu His Leu
1               5                   10                  15

Leu Leu Leu Leu Ser Leu His Arg Arg Lys Ser Tyr Ala Gly Tyr
            20                  25                  30

Gln Thr Leu Lys Phe Glu Arg Gln Gly Pro Gly Pro Gly Asn Gly Ile
            35                  40                  45

Asn Asp Glu Asp Leu Gly Gly Met Tyr Gly Leu Leu Leu Gly Gly
        50                  55                  60

Phe Phe Ser Val Met Gly Pro Gly Pro Gly Val Val Ile Val Met Asp
65                  70                  75                  80

Leu Cys Cys Gln Ile Ala Gly Leu Leu Cys Gly Pro Gly Pro Gly Val
                85                  90                  95

Lys Asn Tyr Leu Asn Gln His Leu Lys Lys Ile Ile Asp Arg Ile Lys
            100                 105                 110

His Ser Asn Leu Asn Ala Ile Gly Pro Gly Pro Gly Glu Leu Asp Lys
            115                 120                 125

Val Glu Leu Pro Lys Thr Arg Ala Arg Glu Thr Ser Ser Asp Ile Thr
130                 135                 140

Val Ile Ser Asp Gly Pro Gly Pro Gly Lys Ala Glu Asp Lys Val Val
145                 150                 155                 160

Lys Ala Ala Gln Ile Gln Asp Val Pro Gly Pro Gly Pro Gly Met Val
                165                 170                 175

Ser Ile Cys Cys Gln Gly Thr Ser Leu Gly Gly Phe Glu Gly Pro
            180                 185                 190

Gly Pro Gly Thr Lys Leu Lys Arg Met Gly Tyr Lys Ile Tyr Asn Val
            195                 200                 205

Ile Phe Ala Gly Pro Gly Pro Gly Leu Gly Ser Ser Ile Met Ala Ile
        210                 215                 220

Phe Gly Lys Leu Pro Trp Pro Ala Gly Pro Gly Pro Gly Ile Val Ser
225                 230                 235                 240

Ser Asp Thr Ser Asn Asn Gly Ser Val Ala Glu Glu Asn Gly Pro Gly
                245                 250                 255

Pro Gly Val Asn Gln Glu Asn Leu Gly Leu Ile Asn Phe Trp Lys Lys
            260                 265                 270

Lys Gly Pro Gly Pro Gly His His His His His Ser Ser Phe Val
            275                 280                 285

Val Leu Ser Gly Tyr Phe Pro Pro Tyr Cys Arg Leu Leu Ala Met Gly
        290                 295                 300

Pro Gly Asn Leu Ala Leu Ser Ser Arg Ala Phe Leu Gly Val Phe Pro
305                 310                 315                 320

Leu Ser Pro Lys Glu Cys Lys Val Cys Met Ser Arg Lys Gln Phe Leu
                325                 330                 335

Trp Lys Leu Leu Glu Asp Lys Gln Arg Leu Arg Pro Phe Ala Gly Ser
            340                 345                 350

Gly Thr Pro His Leu Ala Thr Gly Ala Ser Ala Ala Lys Ser His Val
        355                 360                 365

Tyr Lys Ile His Leu Gln Arg Arg His Asn Pro Ser Ala Thr Leu Val
    370                 375                 380

Gly Leu Trp Lys Glu Ser Asn Gly Ser Pro Gln Ala Tyr Ser Thr Arg
385                 390                 395                 400

Gly Arg Met Pro Arg Arg Tyr Pro Ile Val Trp Asp Leu Ile Trp Gly
                405                 410                 415

Leu Gly Ala His Ala Leu His Val Phe Ser Arg Gly Lys Thr Ser Arg
            420                 425                 430

Pro Pro Glu Pro Arg Gly Arg Gly Phe Pro Leu Lys Val Thr Leu Met
        435                 440                 445

Gln Ile Phe Val Lys Thr Leu Thr Gly Lys Thr Ile Thr Leu Glu Val
    450                 455                 460

Glu Pro Ser Asp Thr Ile Glu Asn Val Lys Ala Lys Ile Gln Asp Lys
465                 470                 475                 480

Glu Gly Ile Pro Pro Asp Gln Gln Arg Leu Ile Phe Ala Gly Lys Gln
                485                 490                 495

Leu Glu Asp Gly Arg Thr Leu Ser Asp Tyr Asn Ile Gln Lys Glu Ser
            500                 505                 510

Thr Leu His Leu Val Leu Arg Leu Arg Gly Ala Met Arg Thr Pro Ala
        515                 520                 525

Gln Phe Leu Gly Ile Leu Leu Leu Trp Phe Pro Gly Ile Lys Cys Ala
    530                 535                 540

Ala Tyr Asp Ile Arg Ala Ile Leu Ser Val Asp Gly Leu Phe Asp Ser
545                 550                 555                 560

Lys Ala Ala Ala Tyr Lys Asn Arg Thr Ile Asn Ile Gly Val Glu Phe
                565                 570                 575

Arg Ile Gln Asp Gly Ala Ala Tyr His Asp Asn Leu Asn Thr Lys Glu
            580                 585                 590

Leu Ser Ile Ser Leu Arg Ile Lys Ala Ala Tyr Ile Pro Gln Glu Lys
        595                 600                 605

Val Ile Ile Leu Asn Arg Phe Leu Gln Asp Tyr Ala Ala Tyr His His
    610                 615                 620

His His His His Ser Ser Phe Val Val Leu Ser
625                 630                 635

<210> SEQ ID NO 5
<211> LENGTH: 1587
<212> TYPE: DNA
<213> ORGANISM: Artificial Sequence
<220> FEATURE:
<223> OTHER INFORMATION: pSignal plus nucleotide sequence

<400> SEQUENCE: 5
atggcccgag ccgcgaaccc cgcccccggg ctcctcggcg ccgcgatgct gctcctgctc      60
ctggtggccg ccggccggcg cgcagcaggg gcgcccgtga ggaggaagag ctacgccggc     120
taccagaccc tggaattgga caaggtggag cttcccaaaa caagggccag agaaacttct     180
agcgatatca ccgtgatcag cgacggccct ggcccgggaa aggccgagga taaggtggtg     240
aaggcggcac agattcagga cgtgccgggc ccaggtccgg gagtcgtgtc catatgttgc     300
cagggcacat cactgggagg attttctgag ggaccgggac caggtactaa attgaagagg     360

```
atggggtaca agatttacaa cgtgatcttc gctggacccg gtccaggcct tgggtcctcc      420
atcatggcca tattcggcaa gctcccatgg ccagccggac ccgtccagg gatcgtcagc       480 tccgacactt ctaataacgg tagcgtggcc gaagagaacg ggcccggccc cggagtcaat      540
caggagaacc tcggcctcat caacttctgg aaaaagaaac accatcatca tcaccactga      600
tcgtcgtttg tcgttttgtc gttggttatt ttccaccata ttgccgtctt ttggcaatgt     660
gagggcccgg aaacctggcc ctgtcttctt gacgagcatt cctagggtc tttcccctct      720 cgccaaagga atgcaaggtc tgttgaatgt cgtgaaggaa gcagttcctc tggaagcttc     780
ttgaagacaa caacgtctg tagcgaccct ttgcaggcag cggaaccccc cacctggcga      840
caggtgcctc tgcggccaaa agccacgtgt ataagataca cctgcaaagg cggcacaacc    900
ccagtgccac gttgtgagtt ggatagttgt ggaaagagtc aaatggctct cctcaagcgt    960
attcaacaag gggctgaagg atgcccagaa ggtaccccat tgtatgggat ctgatctggg   1020
gcctcggtgc acatgcttta catgtgttta gtcgaggtta aaaacgtct aggcccccg     1080 aaccacgggg acgtggtttt cctttgaaag tttaaacgct agcatgcaaa tatttgtgaa   1140
gacactgact ggcaaaacga ttaccctcga ggtcgaaccc agcgacacca tcgaaaacgt   1200
gaaggctaag atccaggaca aggagggtat accacctgac cagcaacgcc tcatcttcgc   1260
ggggaagcag cttgaggacg gcgcacatt gtccgactat aatatccaga aggagtcaac    1320
gcttcacctg gtgctgagac tgagaggcgc cgacctcaaa acagaacga ttaacatagg    1380 ggtcgaattc cggatccagg acggcgccgc ttaccacgac aatctgaaca ccaaagagtt   1440
gtcaatcagc ctccgcatca aagccgccta cattccgcag gagaaggtga tcatccttaa   1500
caggttcctg caggactatg ttaaccagga aaacctggga ctgcaccacc accatcacca   1560
ctaatcgtcg tttgtcgttt tgtcgtt                                         1587

<210> SEQ ID NO 6
<211> LENGTH: 1491
<212> TYPE: DNA
<213> ORGANISM: Artificial Sequence
<220> FEATURE:
<223> OTHER INFORMATION: pLamp nucleotide sequence

<400> SEQUENCE: 6
atgaggagga agagctacgc cggctaccag accctggaat tggacaaggt ggagcttccc     60
aaaacaaggg ccagagaaac ttctagcgat atcaccgtga tcagcgacgg ccctggcccg    120
ggaaaggccg aggataaggt ggtgaaggcg gcacagattc aggacgtgcc gggcccaggt    180
ccgggagtcg tgtccatatg ttgccagggc acatcactgg gaggattttc tgagggaccg    240
ggaccaggta ctaaattgaa gaggatgggg tacaagattt acaacgtgat cttcgctgga    300
cccggtccag gccttgggtc ctccatcatg gccatattcg gcaagctccc atggccagcc    360
ggacccggtc cagggatcgt cagctccgac acttctaata acggtagcgt ggccgaagag    420
aacgggcccg gccccggagt caatcaggag aacctcggcc tcatcaactt ctggaaaaag    480
aaacaccatc atcatcacca ctgatcgtcg tttgtcgttt tgtcgttggt tattttccac    540
catattgccg tcttttggca atgtgagggc ccggaaacct ggccctgtct tcttgacgag    600
cattcctagg ggtctttccc ctctcgccaa aggaatgcaa ggtctgttga atgtcgtgaa    660
ggaagcagtt cctctggaag cttcttgaag acaacaacg tctgtagcga ccctttgcag    720
gcagcggaac cccccacctg cgacaggtg cctctgcggc aaaagccac gtgtataaga     780 tacacctgca aaggcggcac aaccccagtg ccacgttgtg agttggatag ttgtggaaag    840
```

```
agtcaaatgg ctctcctcaa gcgtattcaa caaggggctg aaggatgccc agaaggtacc      900
ccattgtatg ggatctgatc tggggcctcg gtgcacatgc tttacatgtg tttagtcgag      960
gttaaaaaac gtctaggccc cccgaaccac ggggacgtgg ttttcctttg aaagtttaaa     1020
cgctagcatg caaatatttg tgaagacact gactggcaaa acgattaccc tcgaggtcga     1080
acccagcgac accatcgaaa acgtgaaggc taagatccag gacaaggagg gtataccacc     1140
tgaccagcaa cgcctcatct tcgcggggaa gcagcttgag gacgggcgca cattgtccga     1200
ctataatatc cagaaggagt caacgcttca cctggtgctg agactgagag gcgccgacct     1260
caaaaacaga acgattaaca tagggtcga attccggatc caggacggcg ccgcttacca     1320
cgacaatctg aacaccaaag agttgtcaat cagcctccgc atcaaagccg cctacattcc     1380
gcaggagaag gtgatcatcc ttaacaggtt cctgcaggac tatgttaacc aggaaaacct     1440
gggactgcac caccaccatc accactaatc gtcgtttgtc gttttgtcgt t              1491

<210> SEQ ID NO 7
<211> LENGTH: 1316
<212> TYPE: DNA
<213> ORGANISM: Artificial Sequence
<220> FEATURE:
<223> OTHER INFORMATION: pME1 nucleotide sequence

<400> SEQUENCE: 7
tcgtcgtttg tcgttttgtc gttatgtcct ctctttccat acttcacttg ttgttgttat       60
tgttgtcact tcataggagg aagagctacg ccggctacca gaccctgaaa tttgagaggc      120
agggccccgg ccccggcaac ggtattaatg acgaagacct gggcggcatg tacgggctcc      180
tgctcttggg aggattcttt agtgtgatgg gccccggccc cggcgttgtt atcgttatgg      240
atctgtgttg tcaaatcgcc ggtcttctct gtggccccgg ccccggcgtg aaaaactatc      300
tgaatcagca tctcaagaag attatcgacc gcatcaagca ttctaacctc aacgctatcg      360
gccccggccc cggccatcat catcatcatc attgatcgtc gtttgtcgtt ttgtcgttgg      420 ttatttttcca ccatattgcc gtcttttggc aatgtgaggg cccggaaacc tggccctgtc      480
ttcttgacga gcattcctag gggtcttttcc cctctcgcca aaggaatgca aggtctgttg      540
aatgtcgtga aggaagcagt tcctctggaa gcttcttgaa gacaaacaac gtctgtagcg      600 acccctttgca ggcagcggaa ccccccacct ggcgacaggt gcctctgcgg ccaaaagcca      660
cgtgtataag atacacctgc aaaggcggca caaccccagt gccacgttgt gagttggata      720
gttgtggaaa gagtcaaatg gctctcctca agcgtattca acaaggggct gaaggatgcc      780
cagaaggtac cccattgtat gggatctgat ctggggcctc ggtgcacatg ctttacatgt      840
gtttagtcga ggttaaaaaa cgtctaggcc cccgaaccag cggggacgtg gttttccttt      900
gaaagtttaa acgctagcat gcaaatattt gtgaagacac tgactggcaa aacgattacc      960
ctcgaggtcg aacccagcga caccatcgaa aacgtgaagg ctaagatcca ggacaaggag     1020
ggtataccac ctgaccagca acgcctcatc ttcgcgggga gcagcttga ggacgggcgc      1080 acattgtccg actataatat ccagaaggag tcaacgcttc acctggtgct gagactgaga     1140
ggcgccatgc gcaccccgc acagttcctt ggtattctgc tgctctggtt ccctggtata      1200
aaatgtgccg cttacgacat cagagcgatt ctgtccgtgg acgggctgtt tgacagcaag     1260
gccgccgctt accatcatca tcatcatcat tgatcgtcgt ttgtcgtttt gtcgtt         1316

<210> SEQ ID NO 8
```

<211> LENGTH: 1988
<212> TYPE: DNA
<213> ORGANISM: Artificial Sequence
<220> FEATURE:
<223> OTHER INFORMATION: pME2 nucleotide sequence

<400> SEQUENCE: 8

```
tcgtcgtttg tcgttttgtc gttatgtcct ctctttccat acttcacttg ttgttgttat      60
tgttgtcact tcataggagg aagagctacg ccggctacca gaccctgaaa tttgagaggc     120
agggccccgg ccccggcaac ggtattaatg acgaagacct gggcggcatg tacgggctcc     180
tgctcttggg aggattcttt agtgtgatgg gccccggccc cggcgttgtt atcgttatgg     240
atctgtgttg tcaaatcgcc ggtcttctct gtggccccgg ccccggcgtg aaaaactatc     300
tgaatcagca tctcaagaag attatcgacc gcatcaagca ttctaacctc aacgctatcg     360
gccccggccc cggcgagctg ataaagtgg aactgcccaa gacccgggcc cgcgagactt     420
ccggccccgg ccccggcaag acccgcgcaa gagaaacttc ctccgacatc actgtgatat     480
ctgacggccc cggccccggc aaagctgagg ataaggttgt gaaggcggca cagatacaag     540
acgtgccagg ccccgccccc ggcatggtga gtatctgttg ccaaggcact agccttgggg     600
gcttcagtga gggccccggc cccggcacaa agctcaagcg gatggggtat aagatctata     660
atgtgatctt tgccggcccc ggccccggct ggggagtag catcatggca atattcggca     720
aactgccttg gccagctggc cccggccccg gcatcgtgag cagcgatact ccaacaacg     780
gcagtgtggc tgaggagaac ggccccggcc ccggcgtcaa ccaagagaac ctggggctca     840
ttaacttttg gaagaagaaa ggccccgcc ccggccatca tcatcatcat cattgatcgt     900
cgtttgtcgt tttgtcgttg gttatttttc c accatattgc cgtctttgg caatgtgagg     960
gcccggaaac ctggccctgt cttcttgacg agcattccta ggggtctttc ccctctcgcc    1020
aaaggaatgc aaggtctgtt gaatgtcgtg aaggaagcag ttcctctgga agcttcttga    1080
agacaaacaa cgtctgtagc gaccctttgc aggcagcgga accccccacc tggcgacagg    1140
tgcctctgcg gccaaaagcc acgtgtataa gatacacctg caaaggcggc acaaccccag    1200
tgccacgttg tgagttggat agttgtggaa agagtcaaat ggctctcctc aagcgtattc    1260
aacaagggc tgaaggatgc ccagaaggta ccccattgta tgggatctga tctggggcct    1320
cggtgcacat gctttacatg tgtttagtcg aggttaaaaa acgtctaggc ccccgaacc    1380
acggggacgt ggtttccctt tgaaagttta acgctagca tgcaaatatt tgtgaagaca    1440
ctgactggca aaacgattac cctcgaggtc gaacccagcg acaccatcga aaacgtgaag    1500
gctaagatcc aggacaagga gggtatacca cctgaccagc aacgcctcat cttcgcgggg    1560
aagcagcttg aggacgggcg cacattgtcc gactataata tccagaagga gtcaacgctt    1620
cacctggtgc tgagactgag aggcgccatg cgcaccccg cacagttcct tggtattctg    1680
ctgctctggt tccctggtat aaaatgtgcc gcttacgaca tcagagcgat tctgtccgtg    1740
gacgggctgt ttgacagcaa ggccgccgct tacaaaaatc gcaccattaa catcggagtc    1800
gagttccgaa tccaagacgg tgccgcttac cacgacaacc ttaacacaaa ggaattgtcc    1860
atctctctgc gcatcaaggc cgcttacatc cctcaagaaa aagtcatcat cctgaacagg    1920
tttctccaag attacgccgc ttaccatcat catcatcatc attgatcgtc gtttgtcgtt    1980
ttgtcgtt                                                             1988
```

<210> SEQ ID NO 9
<211> LENGTH: 16

```
<212> TYPE: PRT
<213> ORGANISM: Artificial Sequence
<220> FEATURE:
<223> OTHER INFORMATION: Erum7140-p6 CD4 peptide sequence

<400> SEQUENCE: 9

Glu Leu Asp Lys Val Glu Leu Pro Lys Thr Arg Ala Arg Glu Thr Ser
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Erum7140-p7 CD4 peptide sequence

<400> SEQUENCE: 10

Lys Thr Arg Ala Arg Glu Thr Ser Ser Asp Ile Thr Val Ile Ser Asp
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Erum7140-p20 CD4 peptide sequence

<400> SEQUENCE: 11

Lys Ala Glu Asp Lys Val Val Lys Ala Ala Gln Ile Gln Asp Val Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Erum7350-p9 CD4 peptide sequence

<400> SEQUENCE: 12

Val Val Ser Ile Cys Cys Gln Gly Thr Ser Leu Gly Gly Phe Ser Glu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Erum7620-p12 CD4 peptide sequence

<400> SEQUENCE: 13

Thr Lys Leu Lys Arg Met Gly Tyr Lys Ile Tyr Asn Val Ile Phe Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Erum8010-p8 CD4 peptide sequence

<400> SEQUENCE: 14

Leu Gly Ser Ser Ile Met Ala Ile Phe Gly Lys Leu Pro Trp Pro Ala
1               5                   10                  15

<210> SEQ ID NO 15
<211> LENGTH: 16
<212> TYPE: PRT
```

```
<213> ORGANISM: Artificial Sequence
<220> FEATURE:
<223> OTHER INFORMATION: Erum7320-p21CD4 peptide sequence

<400> SEQUENCE: 15

Ile Val Ser Ser Asp Thr Ser Asn Asn Gly Ser Val Ala Glu Glu Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Erum2540-p21 CD4 peptide sequence

<400> SEQUENCE: 16

Val Asn Gln Glu Asn Leu Gly Leu Ile Asn Phe Trp Lys Lys Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Erum2540-p6 CD8 peptide sequence

<400> SEQUENCE: 17

Lys Asn Arg Thr Ile Asn Ile Gly Val Glu Phe Arg Ile Gln Asp Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Erum2540-p16 CD8 peptide sequence

<400> SEQUENCE: 18

His Asp Asn Leu Asn Thr Lys Glu Leu Ser Ile Ser Leu Arg Ile Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Erum2540-p19 CD8 peptide sequence

<400> SEQUENCE: 19

Ile Pro Gln Glu Lys Val Ile Ile Leu Asn Arg Phe Leu Gln Asp Tyr
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Erum0660-p42 CD8 peptide sequence

<400> SEQUENCE: 20

Asp Ile Arg Ala Ile Leu Ser Val Asp Gly Leu Phe Asp Ser Lys Ala
1               5                   10                  15

<210> SEQ ID NO 21
<211> LENGTH: 16
<212> TYPE: PRT
<213> ORGANISM: Artificial Sequence
```

<220> FEATURE:
<223> OTHER INFORMATION: Erum5420-p13 CD4 peptide sequence

<400> SEQUENCE: 21

Val Lys Asn Tyr Leu Asn Gln His Leu Lys Lys Ile Ile Asp Arg Ile
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Erum5420-p14 CD4 peptide sequence

<400> SEQUENCE: 22

Leu Lys Lys Ile Ile Asp Arg Ile Lys His Ser Asn Leu Asn Ala Ile
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Erum1150-p18 CD4 peptide sequence

<400> SEQUENCE: 23

Asn Gly Ile Asn Asp Glu Asp Leu Gly Gly Met Tyr Gly Leu Leu Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Erum1150-p19 CD4 peptide sequence

<400> SEQUENCE: 24

Gly Gly Met Tyr Gly Leu Leu Leu Gly Gly Phe Phe Ser Val Met
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Erum7360-p8 CD4 peptide sequence

<400> SEQUENCE: 25

Val Val Ile Val Met Asp Leu Cys Cys Gln Ile Ala Gly Leu Leu Cys
1               5                   10                  15

<210> SEQ ID NO 26
<211> LENGTH: 465
<212> TYPE: DNA
<213> ORGANISM: Artificial Sequence
<220> FEATURE:
<223> OTHER INFORMATION: pSignal plus/pLamp CD4 epitopes codon
      optimised nucleotide sequence

<400> SEQUENCE: 26
gaattggaca aggtggagct tcccaaaaca agggccagag aaacttctag cgatatcacc 60
gtgatcagcg acggccctgg cccgggaaag gccgaggata aggtggtgaa ggcggcacag 120
attcaggacg tgccgggccc aggtccggga gtcgtgtcca tatgttgcca gggcacatca 180
ctgggaggat tttctgaggg accgggacca ggtactaaat tgaagaggat ggggtacaag 240

```
atttacaacg tgatcttcgc tggacccggt ccaggccttg ggtcctccat catggccata      300
ttcggcaagc tcccatggcc agccggaccc ggtccaggga tcgtcagctc cgacacttct      360
aataacggta gcgtggccga agagaacggg cccggcccg gagtcaatca ggagaacctc       420
ggcctcatca acttctggaa aaagaaacac catcatcatc accac                     465
```

<210> SEQ ID NO 27
<211> LENGTH: 186
<212> TYPE: DNA
<213> ORGANISM: Artificial Sequence
<220> FEATURE:
<223> OTHER INFORMATION: pSignal plus/pLamp CD8 epitopes codon
      optimised nucleotide sequence

<400> SEQUENCE: 27

```
aaaaacagaa cgattaacat aggggtcgaa ttccggatcc aggacggcgc cgcttaccac       60
gacaatctga acaccaaaga gttgtcaatc agcctccgca tcaaagccgc ctacattccg      120
caggagaagg tgatcatcct taacaggttc ctgcaggact atgttaacca ggaaaacctg      180
ggactg                                                                 186
```

<210> SEQ ID NO 28
<211> LENGTH: 318
<212> TYPE: DNA
<213> ORGANISM: Artificial Sequence
<220> FEATURE:
<223> OTHER INFORMATION: pME1 epitopes codon optimised nucleotide
      sequence

<400> SEQUENCE: 28

```
ggccccggcc ccggcaacgg tattaatgac gaagacctgg gcggcatgta cgggctcctg       60
ctcttgggag gattctttag tgtgatgggc cccggcccg cgttgttat cgttatggat       120 ctgtgttgtc aaatcgccgg tcttctctgt ggccccggcc ccggcgtgaa aaactatctg      180
aatcagcatc tcaagaagat tatcgaccgc atcaagcatt ctaacctcaa cgctatcggc      240
cccggccccg cgccgcctta cgacatcaga gcgattctgt ccgtggacgg gctgtttgac      300
agcaaggccg ccgcttac                                                    318
```

<210> SEQ ID NO 29
<211> LENGTH: 99
<212> TYPE: DNA
<213> ORGANISM: Artificial Sequence
<220> FEATURE:
<223> OTHER INFORMATION: CXCL1 signal nt sequence

<400> SEQUENCE: 29

```
atggcccgag ccgcgaaccc cgcccccgg ctcctcggcg ccgcgatgct gctcctgctc       60
ctggtggccg ccggccggcg cgcagcaggg gcgcccgtg                             99
```

<210> SEQ ID NO 30
<211> LENGTH: 32
<212> TYPE: PRT
<213> ORGANISM: Artificial Sequence
<220> FEATURE:
<223> OTHER INFORMATION: CXCL1 signal aa sequence

<400> SEQUENCE: 30

```
Ala Arg Ala Ala Asn Pro Ala Pro Arg Leu Leu Gly Ala Ala Met Leu
1               5                   10                  15

Leu Leu Leu Leu Val Ala Ala Gly Arg Arg Ala Ala Gly Ala Pro Val
            20                  25                  30
```

<210> SEQ ID NO 31
<211> LENGTH: 33
<212> TYPE: DNA
<213> ORGANISM: Artificial Sequence
<220> FEATURE:
<223> OTHER INFORMATION: LAMP nt sequence

<400> SEQUENCE: 31
aggaggaaga gctacgccgg ctaccagacc ctg                                    33

<210> SEQ ID NO 32
<211> LENGTH: 11
<212> TYPE: PRT
<213> ORGANISM: Artificial Sequence
<220> FEATURE:
<223> OTHER INFORMATION: LAMP amino acid sequence

<400> SEQUENCE: 32

Arg Arg Lys Ser Tyr Ala Gly Tyr Gln Thr Leu
1               5                   10

<210> SEQ ID NO 33
<211> LENGTH: 23
<212> TYPE: DNA
<213> ORGANISM: Artificial Sequence
<220> FEATURE:
<223> OTHER INFORMATION: CpG motif nt sequence

<400> SEQUENCE: 33
tcgtcgtttg tcgttttgtc gtt                                               23

<210> SEQ ID NO 34
<211> LENGTH: 499
<212> TYPE: DNA
<213> ORGANISM: Artificial Sequence
<220> FEATURE:
<223> OTHER INFORMATION: IRES nt sequence

<400> SEQUENCE: 34
ggttattttc caccatattg ccgtcttttg gcaatgtgag ggcccggaaa cctggccctg        60
tcttcttgac gagcattcct aggggtcttt ccctctcgc caaaggaatg caaggtctgt       120
tgaatgtcgt gaaggaagca gttcctctgg aagcttcttg aagacaaaca acgtctgtag      180
cgaccctttg caggcagcgg aaccccccac ctggcgacag gtgcctctgc ggccaaaagc      240
cacgtgtata agatacacct gcaaaggcgg cacaacccca gtgccacgtt gtgagttgga      300
tagttgtgga aagagtcaaa tggctctcct caagcgtatt caacaagggg ctgaaggatg      360
cccagaaggt accccattgt atgggatctg atctggggcc tcggtgcaca tgctttacat      420
gtgtttagtc gaggttaaaa aacgtctagg ccccccgaac cacggggacg tggttttcct      480
ttgaaagttt aaacgctag                                                   499

<210> SEQ ID NO 35
<211> LENGTH: 234
<212> TYPE: DNA
<213> ORGANISM: Artificial Sequence
<220> FEATURE:
<223> OTHER INFORMATION: Ubiquitin signal nt sequence

<400> SEQUENCE: 35
atgcaaatat tgtgtgaagac actgactggc aaaacgatta ccctcgaggt cgaacccagc       60
gacaccatcg aaaacgtgaa ggctaagatc caggacaagg agggtatacc acctgaccag      120

```
caacgcctca tcttcgcggg gaagcagctt gaggacgggc gcacattgtc cgactataat    180
atccagaagg agtcaacgct tcacctggtg ctgagactga gaggcgccga cctc          234
```

<210> SEQ ID NO 36
<211> LENGTH: 78
<212> TYPE: PRT
<213> ORGANISM: Artificial Sequence
<220> FEATURE:
<223> OTHER INFORMATION: Ubiquitin signal aa sequence

<400> SEQUENCE: 36

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Asp Leu
65                  70                  75
```

<210> SEQ ID NO 37
<211> LENGTH: 84
<212> TYPE: DNA
<213> ORGANISM: Artificial Sequence
<220> FEATURE:
<223> OTHER INFORMATION: IL-3 sheep signal nt sequence

<400> SEQUENCE: 37

```
atgtcctctc tttccatact tcacttgttg ttgttattgt tgtcacttca taggaggaag    60
agctacgccg gctaccagac cctg                                            84
```

<210> SEQ ID NO 38
<211> LENGTH: 29
<212> TYPE: PRT
<213> ORGANISM: Artificial Sequence
<220> FEATURE:
<223> OTHER INFORMATION: IL-3 sheep signal aa sequence

<400> SEQUENCE: 38

```
Met Met Ser Ser Leu Ser Ile Leu His Leu Leu Leu Leu Leu Leu Ser
1               5                   10                  15

Leu His Arg Arg Lys Ser Tyr Ala Gly Tyr Gln Thr Leu
            20                  25
```

<210> SEQ ID NO 39
<211> LENGTH: 15
<212> TYPE: DNA
<213> ORGANISM: Artificial Sequence
<220> FEATURE:
<223> OTHER INFORMATION: KFERQ lysosome targeting nt sequence

<400> SEQUENCE: 39

```
aaatttgaga ggcag                                                      15
```

<210> SEQ ID NO 40
<211> LENGTH: 5
<212> TYPE: PRT
<213> ORGANISM: Artificial Sequence
<220> FEATURE:
<223> OTHER INFORMATION: KFERQ lysosome targeting peptide sequence

<400> SEQUENCE: 40

Lys Phe Glu Arg Gln
1               5

<210> SEQ ID NO 41
<211> LENGTH: 60
<212> TYPE: DNA
<213> ORGANISM: Artificial Sequence
<220> FEATURE:
<223> OTHER INFORMATION: Ig Kappa signal nt sequence

<400> SEQUENCE: 41
atgcgcaccc ccgcacagtt ccttggtatt ctgctgctct ggttccctgg tataaaatgt    60

<210> SEQ ID NO 42
<211> LENGTH: 20
<212> TYPE: PRT
<213> ORGANISM: Artificial Sequence
<220> FEATURE:
<223> OTHER INFORMATION: Ig Kappa signal peptide

<400> SEQUENCE: 42

Met Arg Thr Pro Ala Gln Phe Leu Gly Ile Leu Leu Leu Trp Phe Pro
1               5                   10                  15

Gly Ile Lys Cys
            20

<210> SEQ ID NO 43
<211> LENGTH: 18
<212> TYPE: DNA
<213> ORGANISM: Artificial Sequence
<220> FEATURE:
<223> OTHER INFORMATION: His tag nt sequence

<400> SEQUENCE: 43
catcatcatc atcatcat                                                  18

<210> SEQ ID NO 44
<211> LENGTH: 6
<212> TYPE: PRT
<213> ORGANISM: Artificial Sequence
<220> FEATURE:
<223> OTHER INFORMATION: His tag aa sequence

<400> SEQUENCE: 44

His His His His His His
1               5

<210> SEQ ID NO 45
<211> LENGTH: 5
<212> TYPE: PRT
<213> ORGANISM: Artificial Sequence
<220> FEATURE:
<223> OTHER INFORMATION: GPGPG spacer peptide sequence

<400> SEQUENCE: 45

Gly Pro Gly Pro Gly
1               5

<210> SEQ ID NO 46
<211> LENGTH: 15
<212> TYPE: DNA
<213> ORGANISM: Artificial Sequence
<220> FEATURE:
<223> OTHER INFORMATION: pSignal plus GPGPG nt sequence (1)

```
<400> SEQUENCE: 46
ggccctggcc cggga                                                    15

<210> SEQ ID NO 47
<211> LENGTH: 15
<212> TYPE: DNA
<213> ORGANISM: Artificial Sequence
<220> FEATURE:
<223> OTHER INFORMATION: SEQ ID NO:47 - pSignal plus GPGPG nt sequence
      (2)

<400> SEQUENCE: 47
ggcccaggtc cggga                                                    15

<210> SEQ ID NO 48
<211> LENGTH: 15
<212> TYPE: DNA
<213> ORGANISM: Artificial Sequence
<220> FEATURE:
<223> OTHER INFORMATION: pSignal plus GPGPG nt sequence (3)

<400> SEQUENCE: 48
ggaccgggac caggt                                                    15

<210> SEQ ID NO 49
<211> LENGTH: 15
<212> TYPE: DNA
<213> ORGANISM: Artificial Sequence
<220> FEATURE:
<223> OTHER INFORMATION: pSignal plus GPGPG nt sequence (4)

<400> SEQUENCE: 49
ggacccggtc caggc                                                    15

<210> SEQ ID NO 50
<211> LENGTH: 15
<212> TYPE: DNA
<213> ORGANISM: Artificial Sequence
<220> FEATURE:
<223> OTHER INFORMATION: pSignal plus GPGPG nt sequence (5)

<400> SEQUENCE: 50
ggacccggtc caggg                                                    15

<210> SEQ ID NO 51
<211> LENGTH: 15
<212> TYPE: DNA
<213> ORGANISM: Artificial Sequence
<220> FEATURE:
<223> OTHER INFORMATION: pSignal plus GPGPG nt sequence (6)

<400> SEQUENCE: 51
gggcccggcc ccgga                                                    15

<210> SEQ ID NO 52
<211> LENGTH: 9
<212> TYPE: DNA
<213> ORGANISM: Artificial Sequence
<220> FEATURE:
<223> OTHER INFORMATION: pSignal plus AAY nt sequence (1)

<400> SEQUENCE: 52 gccgcttac                                                            9
```

```
<210> SEQ ID NO 53
<211> LENGTH: 9
<212> TYPE: DNA
<213> ORGANISM: Artificial Sequence
<220> FEATURE:
<223> OTHER INFORMATION: pSignal plus AAY nt sequence (2)

<400> SEQUENCE: 53 gccgcctac                                                                  9

<210> SEQ ID NO 54
<211> LENGTH: 15
<212> TYPE: DNA
<213> ORGANISM: Artificial Sequence
<220> FEATURE:
<223> OTHER INFORMATION: pME1 GPGPG spacer nt sequence

<400> SEQUENCE: 54
ggccccggcc ccggc                                                          15

<210> SEQ ID NO 55
<211> LENGTH: 48
<212> TYPE: DNA
<213> ORGANISM: Artificial Sequence
<220> FEATURE:
<223> OTHER INFORMATION: Erum7140-p6 CD4 codon optimised nucleotide
      sequence

<400> SEQUENCE: 55
gaattggaca aggtggagct tcccaaaaca agggccagag aaacttct                      48

<210> SEQ ID NO 56
<211> LENGTH: 48
<212> TYPE: DNA
<213> ORGANISM: Artificial Sequence
<220> FEATURE:
<223> OTHER INFORMATION: Erum7140-p7 CD4 codon optimised nucleotide
      sequence

<400> SEQUENCE: 56
aaaacaaggg ccagagaaac ttctagcgat atcaccgtga tcagcgac                      48

<210> SEQ ID NO 57
<211> LENGTH: 48
<212> TYPE: DNA
<213> ORGANISM: Artificial Sequence
<220> FEATURE:
<223> OTHER INFORMATION: Erum7140-p20 CD4 codon optimised nucleotide
      sequence

<400> SEQUENCE: 57
aaggccgagg ataaggtggt gaaggcggca cagattcagg acgtgccg                      48

<210> SEQ ID NO 58
<211> LENGTH: 48
<212> TYPE: DNA
<213> ORGANISM: Artificial Sequence
<220> FEATURE:
<223> OTHER INFORMATION: Erum7350-p9 CD4 codon optimised nucleotide
      sequence

<400> SEQUENCE: 58
gtcgtgtcca tatgttgcca gggcacatca ctgggaggat tttctgag                      48

<210> SEQ ID NO 59
<211> LENGTH: 48
<212> TYPE: DNA
```

<210> SEQ ID NO 59
<211> LENGTH: 48
<212> TYPE: DNA
<213> ORGANISM: Artificial Sequence
<220> FEATURE:
<223> OTHER INFORMATION: Erum7620-p12 CD4 codon optimised nucleotide
      sequence

<400> SEQUENCE: 59
actaaattga agaggatggg gtacaagatt tacaacgtga tcttcgct                48

<210> SEQ ID NO 60
<211> LENGTH: 48
<212> TYPE: DNA
<213> ORGANISM: Artificial Sequence
<220> FEATURE:
<223> OTHER INFORMATION: Erum8010-p8 CD4 codon optimised nucleotide
      sequence

<400> SEQUENCE: 60
cttgggtcct ccatcatggc catattcggc aagctcccat ggccagcc                48

<210> SEQ ID NO 61
<211> LENGTH: 48
<212> TYPE: DNA
<213> ORGANISM: Artificial Sequence
<220> FEATURE:
<223> OTHER INFORMATION: Erum7320-p21CD4 codon optimised nucleotide
      sequence

<400> SEQUENCE: 61
atcgtcagct ccgacacttc taataacggt agcgtggccg aagagaac                48

<210> SEQ ID NO 62
<211> LENGTH: 45
<212> TYPE: DNA
<213> ORGANISM: Artificial Sequence
<220> FEATURE:
<223> OTHER INFORMATION: Erum2540-p21 CD4 codon optimised nucleotide
      sequence

<400> SEQUENCE: 62
gtcaatcagg agaacctcgg cctcatcaac ttctggaaaa agaaa                   45

<210> SEQ ID NO 63
<211> LENGTH: 48
<212> TYPE: DNA
<213> ORGANISM: Artificial Sequence
<220> FEATURE:
<223> OTHER INFORMATION: Erum2540-p6 CD8 codon optimised nucleotide
      sequence

<400> SEQUENCE: 63
aaaaacagaa cgattaacat aggggtcgaa ttccggatcc aggacggc                48

<210> SEQ ID NO 64
<211> LENGTH: 48
<212> TYPE: DNA
<213> ORGANISM: Artificial Sequence
<220> FEATURE:
<223> OTHER INFORMATION: Erum2540-p16 CD8 codon optimised nucleotide
      sequence

<400> SEQUENCE: 64
cacgacaatc tgaacaccaa agagttgtca atcagcctcc gcatcaaa                48

<210> SEQ ID NO 65
<211> LENGTH: 48
<212> TYPE: DNA
<213> ORGANISM: Artificial Sequence

```
<220> FEATURE:
<223> OTHER INFORMATION: Erum2540-p19 CD8 codon optimised nucleotide
      sequence

<400> SEQUENCE: 65
attccgcagg agaaggtgat catccttaac aggttcctgc aggactat                    48

<210> SEQ ID NO 66
<211> LENGTH: 48
<212> TYPE: DNA
<213> ORGANISM: Artificial Sequence
<220> FEATURE:
<223> OTHER INFORMATION: Erum0660-p42 CD4 codon optimised nucleotidee
      sequence

<400> SEQUENCE: 66
gacatcagag cgattctgtc cgtggacggg ctgtttgaca gcaaggcc                    48

<210> SEQ ID NO 67
<211> LENGTH: 48
<212> TYPE: DNA
<213> ORGANISM: Artificial Sequence
<220> FEATURE:
<223> OTHER INFORMATION: Erum5420-p13 CD4 codon optimised nucleotide
      sequence

<400> SEQUENCE: 67
gtgaaaaact atctgaatca gcatctcaag aagattatcg accgcatc                    48

<210> SEQ ID NO 68
<211> LENGTH: 48
<212> TYPE: DNA
<213> ORGANISM: Artificial Sequence
<220> FEATURE:
<223> OTHER INFORMATION: Erum5420-p14 CD4 codon optimised nucleotide
      sequence

<400> SEQUENCE: 68
ctcaagaaga ttatcgaccg catcaagcat tctaacctca acgctatc                    48

<210> SEQ ID NO 69
<211> LENGTH: 48
<212> TYPE: DNA
<213> ORGANISM: Artificial Sequence
<220> FEATURE:
<223> OTHER INFORMATION: SEQ ID NO:69 - Erum1150-p18 CD4 codon
      optimised nucleotide sequence

<400> SEQUENCE: 69
aacggtatta atgacgaaga cctgggcggc atgtacgggc tcctgctc                    48

<210> SEQ ID NO 70
<211> LENGTH: 48
<212> TYPE: DNA
<213> ORGANISM: Artificial Sequence
<220> FEATURE:
<223> OTHER INFORMATION: Erum1150-p19 CD4 codon optimised nucleotide
      sequence

<400> SEQUENCE: 70
ggcggcatgt acgggctcct gctcttggga ggattcttta gtgtgatg                    48

<210> SEQ ID NO 71
<211> LENGTH: 48
<212> TYPE: DNA
<213> ORGANISM: Artificial Sequence
<220> FEATURE:
```

```
<223> OTHER INFORMATION: Erum7360-p8 CD8 codon optimised nucleotide
      sequence

<400> SEQUENCE: 71
gttgttatcg ttatggatct gtgttgtcaa atcgccggtc ttctctgt              48

<210> SEQ ID NO 72
<211> LENGTH: 16
<212> TYPE: PRT
<213> ORGANISM: Artificial Sequence
<220> FEATURE:
<223> OTHER INFORMATION: Erum2540-p20 CD8 peptide sequence

<400> SEQUENCE: 72

Leu Asn Arg Phe Leu Gln Asp Tyr Val Asn Gln Glu Asn Leu Gly Leu
1               5                   10                  15

<210> SEQ ID NO 73
<211> LENGTH: 48
<212> TYPE: DNA
<213> ORGANISM: Artificial Sequence
<220> FEATURE:
<223> OTHER INFORMATION: Erum2540-p20 CD8 codon optimised nucleotide
      sequence

<400> SEQUENCE: 73
cttaacaggt tcctgcagga ctatgttaac caggaaaacc tgggactg              48
```